(12) United States Patent
McGinley et al.

(10) Patent No.: US 11,564,698 B2
(45) Date of Patent: Jan. 31, 2023

(54) SENSING OF SURGICAL INSTRUMENT PLACEMENT RELATIVE TO ANATOMIC STRUCTURES

(71) Applicant: McGinley Engineered Solutions, LLC, Casper, WY (US)

(72) Inventors: Joseph C. McGinley, Casper, WY (US); Brian Nolte, Casper, WY (US); Adam M. Johnson, Casper, WY (US); Matthew R. Russell, Casper, WY (US)

(73) Assignee: MCGINLEY ENGINEERED SOLUTIONS, LLC, Casper, WY (US)

(*) Notice: Subject to any disclaimer, the term of this patent is extended or adjusted under 35 U.S.C. 154(b) by 166 days.

(21) Appl. No.: 17/222,168

(22) Filed: Apr. 5, 2021

(65) Prior Publication Data

US 2021/0267608 A1    Sep. 2, 2021

Related U.S. Application Data

(63) Continuation of application No. 16/305,353, filed as application No. PCT/US2018/047847 on Aug. 24, 2018, now Pat. No. 10,987,113.
(Continued)

(51) Int. Cl.
*A61B 17/16* (2006.01)
*A61B 34/00* (2016.01)
*A61B 90/00* (2016.01)

(52) U.S. Cl.
CPC ...... *A61B 17/1626* (2013.01); *A61B 17/1622* (2013.01); *A61B 2034/256* (2016.02);
(Continued)

(58) Field of Classification Search
CPC . A61B 17/16; A61B 17/1615; A61B 17/1617; A61B 17/162; A61B 17/1622;
(Continued)

(56) References Cited

U.S. PATENT DOCUMENTS

| 1,831,813 A | 11/1931 | Levedahl |
| 2,883,891 A | 4/1959 | Robinson et al. |

(Continued)

FOREIGN PATENT DOCUMENTS

| DE | 102011056927 | 6/2017 |
| EP | 3199112 | 10/2019 |

(Continued)

*Primary Examiner* — Eric S Gibson
(74) *Attorney, Agent, or Firm* — Holzer Patel Drennan

(57) ABSTRACT

Systems and methods related to use of a measurement system in conjunction with a powered instrument for determination of the placement of a tool portion relative to the anatomy of a patient utilizing the powered instrument. The measurement system may include a displacement sensor that indicates the relative displacement of the tool portion relative to the anatomy. The system may also include a sensor for monitoring a tool drive signal representative of a tool drive parameter that is characteristic of the tool portion acting on the anatomy. The tool drive signal may be analyzed relative to a given amount of axial displacement as measured by the displacement sensor to avoid false indications of placement based on noise and or other artifacts in the tool drive signal that may result from characteristics of the anatomy and/or operational behaviors of the surgeon utilizing the instrument.

21 Claims, 15 Drawing Sheets

Related U.S. Application Data

(60) Provisional application No. 62/550,423, filed on Aug. 25, 2017.

(52) U.S. Cl.
CPC ... *A61B 2090/061* (2016.02); *A61B 2090/062* (2016.02); *A61B 2090/064* (2016.02); *A61B 2090/066* (2016.02)

(58) Field of Classification Search
CPC ............ A61B 17/1624; A61B 17/1626; A61B 17/1628; A61B 2090/061; A61B 2090/062; A61B 2090/064; A61B 2090/066

See application file for complete search history.

(56) References Cited

U.S. PATENT DOCUMENTS

| | | | |
|---|---|---|---|
| 3,804,544 A | 4/1974 | Adams | |
| 4,014,621 A | 3/1977 | Johnson et al. | |
| 4,063,356 A | 12/1977 | Hepworth | |
| 4,157,231 A | 6/1979 | Phillips | |
| 4,310,269 A * | 1/1982 | Neu | B23B 47/32 408/11 |
| 4,329,092 A | 5/1982 | Ponitzsch et al. | |
| 4,329,095 A * | 5/1982 | Schmuck | B25H 1/0092 408/112 |
| 4,644,335 A | 2/1987 | Wen | |
| 4,710,075 A | 5/1987 | Davison | |
| 4,723,911 A | 2/1988 | Kurtz | |
| 4,765,333 A | 8/1988 | Bray | |
| 4,867,158 A | 9/1989 | Sugg | |
| 4,951,690 A | 8/1990 | Baker | |
| 5,013,194 A | 5/1991 | Wienhold | |
| 5,014,793 A * | 5/1991 | Germanton | H02P 1/18 81/473 |
| 5,022,798 A | 6/1991 | Eckman | |
| 5,071,293 A * | 12/1991 | Wells | B23Q 5/263 408/112 |
| 5,133,728 A | 7/1992 | Petersen | |
| 5,139,376 A * | 8/1992 | Pumphrey | G05B 19/4015 408/1 R |
| 5,161,921 A * | 11/1992 | Corsi | B23Q 9/0014 408/1 R |
| 5,277,799 A | 1/1994 | Bransch | |
| 5,361,504 A | 11/1994 | Huang | |
| 5,380,333 A | 1/1995 | Meloul et al. | |
| 5,411,503 A * | 5/1995 | Hollstien | A61B 17/1707 606/86 R |
| 5,533,842 A * | 7/1996 | Johnson | B23Q 16/003 408/130 |
| 5,538,423 A | 7/1996 | Coss et al. | |
| 5,584,838 A | 12/1996 | Rona et al. | |
| 5,599,142 A * | 2/1997 | Fujimoto | B23Q 15/12 408/6 |
| 5,613,810 A | 3/1997 | Bureller | |
| 5,810,828 A | 9/1998 | Lightman et al. | |
| 5,902,306 A | 5/1999 | Norman | |
| 5,961,257 A | 10/1999 | Bettini et al. | |
| 5,980,248 A | 11/1999 | Kusakabe et al. | |
| 6,033,409 A * | 3/2000 | Allotta | B25F 5/003 606/80 |
| 6,081,741 A | 6/2000 | Hollis | |
| 6,096,042 A * | 8/2000 | Herbert | A61B 17/8891 606/80 |
| 6,342,057 B1 | 1/2002 | Brace et al. | |
| 6,494,590 B1 | 12/2002 | Paganini et al. | |
| 6,527,778 B2 * | 3/2003 | Athanasiou | A61B 10/0233 606/80 |
| 6,587,184 B2 | 7/2003 | Wursch | G01S 17/88 7/163 |
| 6,665,948 B1 * | 12/2003 | Kozin | A61B 90/06 175/45 |
| 6,786,683 B2 * | 9/2004 | Schaer | B23B 49/006 408/8 |
| D502,798 S | 3/2005 | Belley et al. | |
| 6,925,725 B2 * | 8/2005 | Herrmann | B23Q 17/20 408/11 |
| 7,073,989 B2 | 7/2006 | Erickson et al. | |
| 7,185,998 B2 | 3/2007 | Oomori et al. | |
| 7,220,088 B2 | 5/2007 | Ferrari et al. | |
| 7,235,940 B2 * | 6/2007 | Bosch | B25B 23/147 173/4 |
| 7,314,048 B2 | 1/2008 | Couture et al. | |
| 7,482,819 B2 | 1/2009 | Wuersch | |
| 7,578,642 B2 | 8/2009 | Fritsche et al. | |
| 7,681,659 B2 * | 3/2010 | Zhang | B25B 21/00 173/4 |
| 7,691,106 B2 | 4/2010 | Schenberger | |
| 7,840,253 B2 | 11/2010 | Tremblay et al. | |
| 7,946,049 B1 * | 5/2011 | Wilton | G01B 3/30 33/526 |
| 7,992,311 B2 * | 8/2011 | Cerwin | B25H 1/0092 33/286 |
| 8,092,457 B2 * | 1/2012 | Oettinger | A61B 17/1626 606/80 |
| 8,162,074 B2 | 4/2012 | Cook | |
| 8,167,518 B2 * | 5/2012 | Mathis | B23Q 5/225 408/1 R |
| 8,171,642 B2 | 5/2012 | Fritsche et al. | |
| 8,317,437 B2 | 11/2012 | Merkley et al. | |
| 8,460,297 B2 | 6/2013 | Watlington et al. | |
| 8,463,421 B2 | 6/2013 | Brett | |
| 8,511,945 B2 | 8/2013 | Apkarian | |
| 8,734,153 B2 | 5/2014 | Arzanpour et al. | |
| 8,821,493 B2 * | 9/2014 | Anderson | A61B 17/1624 606/171 |
| 8,894,654 B2 * | 11/2014 | Anderson | B23B 49/02 173/176 |
| 8,925,169 B2 * | 1/2015 | Schevers | B23B 49/00 408/139 |
| 9,022,949 B2 | 5/2015 | Herndon | |
| 9,114,494 B1 * | 8/2015 | Mah | B25H 1/0092 |
| 9,204,885 B2 * | 12/2015 | McGinley | A61B 17/162 |
| 9,358,016 B2 * | 6/2016 | McGinley | A61B 17/162 |
| 9,370,372 B2 * | 6/2016 | McGinley | A61B 17/1626 |
| 9,492,181 B2 * | 11/2016 | McGinley | A61B 17/162 |
| 9,826,984 B2 * | 11/2017 | McGinley | A61B 17/142 |
| 9,855,060 B2 * | 1/2018 | Ardel | A61B 17/162 |
| 9,877,734 B2 * | 1/2018 | Anderson | B23B 45/008 |
| 10,149,686 B2 * | 12/2018 | Anderson | A61B 17/17 |
| 10,321,920 B2 * | 6/2019 | McGinley | A61B 17/1633 |
| 10,398,453 B2 * | 9/2019 | McGinley | A61B 90/30 |
| 10,736,644 B2 * | 8/2020 | Windolf | A61B 17/1622 |
| 10,987,113 B2 * | 4/2021 | McGinley | A61B 17/1622 |
| 2001/0031919 A1 | 10/2001 | Strommer et al. | |
| 2001/0047219 A1 * | 11/2001 | Oden | B23Q 17/2233 700/160 |
| 2002/0165549 A1 | 11/2002 | Owusu-Akyaw et al. | |
| 2003/0049082 A1 * | 3/2003 | Morrison | B23B 49/026 408/97 |
| 2003/0229351 A1 | 12/2003 | Tidwell | |
| 2004/0097948 A1 | 5/2004 | Heldreth | |
| 2004/0146367 A1 * | 7/2004 | Gerhardt | B25F 5/003 408/110 |
| 2004/0179829 A1 | 9/2004 | Phillips et al. | |
| 2004/0215395 A1 * | 10/2004 | Strasser | B23B 49/006 702/9 |
| 2005/0116673 A1 * | 6/2005 | Carl | A61B 17/1626 318/432 |
| 2005/0131415 A1 * | 6/2005 | Hearn | B25B 23/147 606/80 |
| 2005/0169717 A1 * | 8/2005 | Field | E21B 47/04 408/16 |
| 2005/0261870 A1 * | 11/2005 | Cramer | G01B 11/22 702/166 |
| 2006/0004371 A1 | 1/2006 | Williams et al. | |
| 2006/0008771 A1 | 1/2006 | Courvoisier | |
| 2006/0025677 A1 | 2/2006 | Verard | |
| 2006/0074292 A1 | 4/2006 | Thomson et al. | |

(56) References Cited

U.S. PATENT DOCUMENTS

| | | |
|---|---|---|
| 2006/0258938 A1 | 11/2006 | Hoffman |
| 2007/0030486 A1* | 2/2007 | Gelbart .............. B23Q 17/2233 356/399 |
| 2007/0035311 A1* | 2/2007 | Wuersch ................ B25D 17/00 324/637 |
| 2007/0041799 A1 | 2/2007 | Schaefer et al. |
| 2008/0119725 A1 | 5/2008 | Lloyd |
| 2008/0167653 A1 | 7/2008 | Watlington et al. |
| 2008/0226409 A1 | 9/2008 | Hasenzahl |
| 2008/0228195 A1 | 9/2008 | von Jako et al. |
| 2008/0243125 A1 | 10/2008 | Guzman et al. |
| 2008/0292416 A1 | 11/2008 | Kado et al. |
| 2009/0131986 A1 | 5/2009 | Lee et al. |
| 2009/0182226 A1 | 7/2009 | Weitzner |
| 2009/0245956 A1* | 10/2009 | Apkarian ................ B23B 49/00 408/11 |
| 2009/0299439 A1* | 12/2009 | Mire ....................... A61B 17/17 606/53 |
| 2009/0326537 A1* | 12/2009 | Anderson .............. A61B 17/17 606/80 |
| 2010/0114099 A1 | 5/2010 | Patwardhan |
| 2010/0137874 A1 | 6/2010 | Kim et al. |
| 2010/0239380 A1 | 9/2010 | Amirov et al. |
| 2011/0020084 A1 | 1/2011 | Brett et al. |
| 2011/0060242 A1 | 3/2011 | Hausman et al. |
| 2011/0245831 A1 | 10/2011 | Giersch et al. |
| 2011/0245832 A1 | 10/2011 | Giersch et al. |
| 2011/0245833 A1* | 10/2011 | Anderson ................ B23B 49/02 606/80 |
| 2011/0301611 A1* | 12/2011 | Garcia ................ A61B 17/8875 606/104 |
| 2012/0123418 A1 | 5/2012 | Giurgi et al. |
| 2012/0179070 A1 | 7/2012 | Pommer et al. |
| 2012/0253348 A1 | 10/2012 | Arlettaz et al. |
| 2013/0122466 A1 | 5/2013 | Connor et al. |
| 2013/0237811 A1 | 9/2013 | Mihailescu et al. |
| 2013/0304069 A1 | 11/2013 | Bono et al. |
| 2013/0307529 A1* | 11/2013 | Baumgartner .......... B23B 49/00 324/207.2 |
| 2013/0327552 A1 | 12/2013 | Lovelass |
| 2014/0039517 A1 | 2/2014 | Stryker |
| 2014/0081659 A1 | 3/2014 | Nawana |
| 2014/0107471 A1 | 4/2014 | Haider et al. |
| 2014/0275760 A1 | 9/2014 | Lee |
| 2014/0275989 A1 | 9/2014 | Jacobsen |
| 2014/0350685 A1 | 11/2014 | Bagga |
| 2015/0066030 A1* | 3/2015 | McGinley .............. A61B 90/30 606/79 |
| 2015/0066035 A1* | 3/2015 | McGinley ............ A61B 17/162 606/80 |
| 2015/0066036 A1* | 3/2015 | McGinley ............ A61B 17/162 606/80 |
| 2015/0066037 A1* | 3/2015 | McGinley .......... A61B 17/1628 606/80 |
| 2015/0066038 A1* | 3/2015 | McGinley .......... A61B 17/1615 606/80 |
| 2015/0165580 A1* | 6/2015 | Holland .............. B23Q 17/2275 408/1 BD |
| 2016/0120553 A1* | 5/2016 | Xie ..................... A61B 17/1628 606/80 |
| 2016/0178343 A1 | 6/2016 | Hale et al. |
| 2016/0247276 A1 | 8/2016 | Chou et al. |
| 2017/0128081 A1* | 5/2017 | McGinley .......... A61B 17/1695 |
| 2017/0143396 A1* | 5/2017 | McGinley .............. A61B 90/06 |
| 2017/0345398 A1 | 11/2017 | Fuchs |
| 2018/0070113 A1 | 3/2018 | Phillips |
| 2018/0110572 A1 | 4/2018 | Flatt |
| 2018/0260931 A1 | 9/2018 | Ozguner |
| 2019/0209287 A1 | 7/2019 | Zens-Olson |
| 2020/0113584 A1* | 4/2020 | McGinley .......... A61B 17/1626 |
| 2021/0267608 A1* | 9/2021 | McGinley .......... A61B 17/1622 |

FOREIGN PATENT DOCUMENTS

| | | |
|---|---|---|
| WO | 9724991 | 7/1997 |
| WO | 2015006296 | 1/2015 |
| WO | 2015014771 | 2/2015 |
| WO | 2015034562 | 3/2015 |
| WO | 2015082904 | 6/2015 |
| WO | 2016207628 | 12/2016 |

\* cited by examiner

SENSING OF SURGICAL INSTRUMENT PLACEMENT RELATIVE TO ANATOMIC STRUCTURES

RELATED APPLICATIONS

This application is continuation of U.S. application Ser. No. 16/305,353, filed on Nov. 28, 2018, which is a National Stage Application under 37 CFR 371 of PCT Application No. PCT/US2018/047847 filed on Aug. 24, 2018 entitled "SENSING OF SURGICAL INSTRUMENT PLACEMENT RELATIVE TO ANATOMIC STRUCTURES", which claims the benefit of U.S. Application No. 62/550,423 filed on Aug. 25, 2017 entitled "SENSING OF SURGICAL INSTRUMENT PLACEMENT RELATIVE TO ANATOMIC STRUCTURES", the entirety of which is incorporated by reference herein.

BACKGROUND

The use of powered surgical instruments is common in many surgical procedures. Examples of such instruments may include drills, saws, grinders, or the like that may be electric, pneumatic, hydraulic, or otherwise powered. Often times, use of such powered surgical instruments may allow for more efficient surgical operations, thus resulting in reduced risk to the patient, improved efficiency for the surgeon, and lower costs.

However, while such powered surgical instruments may provide advantages over human powered instruments, there may also be increased risk for inadvertent damage to the anatomy of the patient when using powered instruments. For instance, surgical procedures often require precise placement of tools relative to the anatomy of a patient. In this regard, surgeons may, when using powered instruments, rely solely on the senses of the surgeon to determine when a tool is in a certain position relative to the anatomy of a patient. For instance, when drilling through the bone of a patient, "plunge" may occur when the drill bit used with a drill may erupt from the distal portion of the bone through which a bore is being drilled. A surgeon may be required to anticipate and/or react to plunge to cease operation of the drill to reduce the potential for damage to tissue beyond the bone to be drilled.

However, the use of a surgeon's senses alone to "feel" when a tool in a certain position relative to the anatomy of a patient may have limits. For instance, repeatability may suffer as each patient may present unique anatomy that presents to the surgeon in a different manner. Moreover, as the use of a surgeon's senses alone is highly subjective, certain placements may be more readily and repeatedly achieved by some, but possibly not all, surgeons. Further still, when utilizing powered surgical instruments, the ability for a surgeon to accurately use his or her senses to place a tool relative to the anatomy of a patient may be compromised as the surgical tool may mask or attenuate any available feedback provided to the surgeon when using such instruments. Further still, events related to placement of tools may occur very rapidly, such that reaction times among various surgeons may differ or be too slow to accurately control the operation of the tool. As such, the use of powered surgical instruments, while providing distinct advantages in many operations, continue to suffer from drawbacks that limit the potential benefits of such tools.

SUMMARY

In view of the foregoing, the present application relates to improved sensing for the placement of a tool by a powered surgical instrument relative to the anatomy of a patient. Specifically, the present disclosure utilizes a measurement system in conjunction with a powered surgical instrument to determine the placement of the tool relative to the anatomy of a patient. The measurement system may include or otherwise be in operative communication with a controller to analyze sensor outputs that relate to drive parameters of the tool. The controller may be a computerized system (e.g., including a processor and memory) capable of rapid analysis of the sensor outputs to control operation of the instrument in response to the analysis of the sensor outputs. Prior approaches to such measurement systems have been proposed, such as in U.S. patent application Ser. No. 15/336,202 filed on Oct. 27, 2016 entitled "TECHNIQUES AND INSTRUMENTS FOR PLACEMENT OF ORTHOPEDIC IMPLANTS RELATIVE TO BONE FEATURES," the entirety of which is incorporated herein by reference in its entirety.

In such prior approaches to measurement systems for placement of tools relative to anatomical structures of a patient, a number of sensors that produce sensor outputs corresponding to characteristics of the tool were utilized such that an analysis of the sensor outputs is used to determine placement of the tool. However, in such systems, it may be difficult to accurately determine placement relative to the anatomy for a number of reasons.

For instance, it has been found that the manner in which surgeons use powered instruments may vary in relation to the rate and/or manner at which the instrument is advanced. In turn, the monitored parameters of such systems used to determine instrument placement may be difficult to analyze consistently. For instance, the force used to advance the instrument, whether and the degree to which a surgeon retracts the instrument between periods of advancement (e.g., "pecks"), and other potential variations in use may all may affect the characteristics or parameters monitored by a measurement system in determining the placement of an instrument. It has been found that certain surgeon behaviors may result in false indications of instrument placement.

Moreover, variations in anatomy may also lead to false indications of placement. For instance, different patients may have different anatomical characteristics that are difficult to accurately model when analyzing sensor outputs in a traditional manner. Further still, anatomic structures may not provide sufficient uniformity for modeling using the traditional approaches. As an example, it has been proposed to monitor a force and a displacement signal to determine placement of a tool relative to anatomical structures of a bone of a patient. In such approaches, a medullary layer of the bone has been modeled as a uniformly dense region of the bone that is relatively less dense than the hard outer cortex of the bone. However, in reality trabeculae, which are osseous fibers extending through the medullary may affect the measured parameters or characteristics used to determine placement of the instrument.

In this regard, it may be appreciated that applications exist in which the analysis of sensor data may be difficult in view of any one of the foregoing examples. Namely, these scenarios may include noise in the signals analyzed and/or low magnitude signals. For instance, noise may be created in the signal due to anatomical structure (e.g., trabeculations as described above), mechanical vibration of the instrument as it operates, mechanical binding of the tool relative to the anatomy of the patient, or the like. Furthermore, electrically induced noise, while preferably minimized by the design of the electronic components of the instrument/controller, may still be present. In any regard, the result may include reduced signal to noise ratios that make accurately analyzing signal to detect instrument placement more difficult.

However, a number of approaches are described herein that may assist in such signal analysis to improve accuracy of instrument placement even in noisy contexts with relatively low signal to noise ratios. The approaches described herein may be applied to any or all of the signals analyzed in the system. In a particular application, a tool drive parameter may be measured by a sensor to output a tool drive signal, upon which the approaches described herein may be used. Specifically, the tool drive parameter may be monitored for a change in the tool drive parameter (e.g., to detect an increase or decrease in force associated with the tool portion of an instrument passing from one medium to another). Such a tool drive parameter may include, for example, an axial force acting on the tool, a torque acting on the tool, or an electrical characteristic of a drive motor of the powered surgical instrument (e.g., a resistance, power, load, or other measure of the drive motor). Appropriate sensors may be provided for measuring or monitoring any of the foregoing tool drive parameters and outputting the tool drive parameter including force sensors, torque sensors, or other measurement sensors.

The approaches described herein may all act to identify a change in the tool drive parameter over a given amount of axial displacement of the tool portion. The change in the tool drive parameter may be indicative of a tool portion of the instrument acting on a different medium of anatomy (e.g., passing from one layer of a bone to another). In this regard, the change in the tool drive parameter may be measured relative to the given amount of axial displacement. Specifically, changes in the tool drive parameter that are not sustained over the given amount of axial displacement may not be identified by the controller as actually corresponding to the tool portion passing from one medium to another. Such changes in the tool drive parameter occurring over distances less than the given amount of axial displacement may be the result of noise, operator behavior, or anatomical structures (e.g., trabeculations). In any regard, such changes in the tool drive parameter occurring over distances less than the given amount of axial displacement are preferably disregarded to avoid false detection of placement of the tool portion. In this regard, approaches described herein may analyze a tool drive parameter in relation to axial displacement rather than relative to time. Accordingly, any such analysis to determine a change in a tool drive parameter may be conducted without respect to time. Such an approach may include collecting tool drive parameter data for each increment of axial displacement that is greater than a previous value. That is, if the tool portion is retracted and readvanced, any data collected during the readvancement of the tool portion may be disregarded such that only the first instance of axial displacement includes tool drive parameter data collection.

A first approach to analysis of the signal may include filtering the signal such that variation within the signal that occurs in an axial displacement less than the given amount of axial displacement are removed from the signal. In this regard, a low pass filter may be provided that removes portions of the signal at relatively high frequencies. The filter may be implemented in hardware or software. Moreover, a cutoff frequency of the filter may be tuned in view of the given amount of axial displacement or other displacement signal.

Another approach described herein relates to determining an integral value of the tool drive parameter. This may include summing the tool drive parameter over a plurality of instances of the given amount of axial displacement. As may be appreciated, the tool drive parameter signal may be plotted relative to the axial displacement of the tool portion. In turn, the integral of the signal relative to the axial displacement may provide the area under the curve plotted and represent a summation of the signal over a given distance. This integral value of the tool drive parameter may be referred to as an integrated tool drive parameter representative of a summation of the drive parameter over a plurality of increments of axial displacement. In turn, an integral threshold value may be established such that the change in the tool drive parameter is identified when the integrated tool drive parameter exceeds the integral threshold. In the event that the integrated tool drive parameter for any given integral window over which the tool drive parameter is summed is less than the integral threshold, no change may be detected in the given integral window. This may be despite local increases or decreases in the tool drive parameter over the integral window. However, once an integral window includes an integrated tool drive parameter exceeds the integral threshold, the change in the tool drive signal may be identified in accordance with any applicable tool placement modality active at the instrument.

Still another approach includes calculation of a moving average of the tool drive parameter. This may act to smooth the tool drive parameter. The moving average may be calculated over the given amount of axial displacement such that spikes in the tool drive parameter that occur over a very short axial displacement (e.g., noise) may not significantly alter the moving average of the tool drive parameter. In turn, the moving average may be analyzed to determine a change in the moving average that is indicative of the tool portion moving from a first medium to a second medium. As will be described in greater detail below, this may include monitoring for an inflection point in the moving average that may indicate the tool portion moving from a harder material to a softer material or from a softer material to a harder material.

In another approach related to moving averages of the tool drive parameter, a first and second moving average may be determined. One of the moving averages may be a relatively short term moving average calculated with fewer values of the tool drive parameter reflecting changes over a shorter axial displacement. In contrast, the other moving average may be a relatively long term moving average calculated with more vales of the tool drive parameter over a greater distance of axial displacement. In turn, a change of the first signal relative to the second signal may be identified that may indicate the tool portion moving from a first to a second medium. As will be appreciated in the discussion to follow, any of the foregoing approaches may be used, potentially in combination, and potentially with other analysis techniques to assist in identifying placement of a tool portion.

Accordingly, a first aspect of the present disclosure includes a measurement system for use with a powered surgical instrument for sensing a position of a leading edge of a tool relative to anatomic structures of a patient. The measurement system includes a first sensor disposed with respect to the powered surgical instrument to measure a tool drive parameter that is characteristic of the tool portion acting on the patient. The first sensor also outputs a tool drive signal representative the tool drive parameter as the tool is advanced relative to anatomy of the patient. The measurement system also includes a displacement sensor disposed with respect to the powered surgical instrument to measure an axial displacement of the leading edge of the tool relative to a reference point. The displacement sensor also outputs a displacement signal representative of the axial displacement. The measurement system further includes a controller in operative communication with the first sensor to receive the tool drive signal and in operative communication with the displacement sensor to receive the displacement signal. The controller is operative to identify a change in the tool drive parameter over a given amount of axial displacement of the leading edge of the tool that is indicative of the leading edge of the tool moving through an interface between anatomic structures of the patient.

A number of feature refinements and additional features are applicable to the first aspect. These feature refinements and additional features may be used individually or in any combination. As such, each of the following features that will be discussed may be, but are not required to be, used with any other feature or combination of features of the first aspect.

In an embodiment, the given amount of axial displacement of the leading edge of the tool may be at least about 0.5 mm. In other embodiments, the given amount of axial displacement may be at least about 1.0 mm, 1.5 mm, 2.0 mm, 2.5 mm, or even 3.0 mm.

When it is determined that the tool portion is placed relative to the anatomy of interested (which may be determined based on a mode selection of the instrument), a number of actions may be performed by the controller. For instance, the controller may be in control of the operation of a drive motor of the powered surgical instrument and may be operative to stop the drive motor in response to identifying the interface between anatomic structures of the patient. Additionally or alternatively, the controller may output a visual, auditory, or other type of alert and/or record a measurement of the displacement of the tool portion at the identified position.

In various embodiments, the first sensor may correspond to one or more sensors for measuring a tool drive parameter. The tool drive parameter may include one of an axial force acting on the tool, a torque acting on the tool, or an electrical characteristic of a drive motor of the powered surgical instrument (e.g., a resistance, power, load, or other measure of the drive motor). Appropriate sensors may be provided for measuring or monitoring any of the foregoing tool drive parameters including force sensors, torque sensors, or other measurement sensors.

For example, the anatomic structures of the patient have different densities. Accordingly, the change in the tool drive parameter may correspond to the working portion of the instrument passing from one anatomical structure (e.g., a first medium) to another anatomical structure (e.g., a second medium). As the working tool begins to operate in the different anatomical structure with a different density, the tool drive parameter may also change, which may be detected.

In a first approach, the controller may be operative to filter the tool drive signal relative to the given mount of axial displacement of the leading edge of the tool portion. Accordingly, changes in the tool drive parameter over distances less than the given amount of axial displacement are not identified as indicative of the leading edge of the tool portion moving through the interface between anatomic structures of the patient. The controller may comprise a filter embodied in either hardware or software for these purposes as will be described in greater detail below.

In another approach, the controller may be operative to determine a moving average for the tool drive parameter with respect to the axial displacement of the leading edge of the tool portion relative to the anatomy of the patient. The controller may be operative to identify the change in the tool drive parameter relative to a given amount of axial displacement of the leading edge of the tool portion based on an inflection of the moving average.

For instance, the interface may be from a medullary layer of a bone to a cortex layer of the bone. As such, the moving average may include an inflection from a minimum of the moving average over the given amount of axial displacement of the leading edge of the tool. Alternatively, the interface may be from a cortex layer of a bone to an exterior of the bone. In this case, the moving average may include an inflection from a maximum of the moving average over the given amount of axial displacement of the leading edge of the tool.

In another embodiment, the interface through which the leading edge of the tool moves may be from a medullary layer of a bone to a cortex layer of the bone. In this embodiment, one approach to detecting a change in the tool drive parameter may include the controller operating to determine an integrated tool drive parameter comprising a sum of the tool drive parameter over a given plurality of instances of the given amount of axial displacement of the leading edge of the tool portion. The controller may be operative to compare the integrated tool drive parameter to an integral threshold value and identify the change in the tool drive parameter when the integrated tool drive parameter exceeds the integral threshold value. The given plurality of instances of the given amount of axial displacement of the leading edge of the tool portion may comprise the immediately preceding instances of the given amount of axial displacement to a current position of the leading edge of the tool portion. In an example of this approach, the given amount of axial displacement may comprise 0.1 mm and the given plurality of instances may comprise ten instances.

In another approach, the controller may be operative to generate a short term moving average for the tool drive parameter with respect to a first axial displacement of the leading edge of the tool portion relative to the anatomy of the patient and generate a long term moving average for the tool drive parameter with respect to a second axial displacement of the leading edge of the tool portion relative to the anatomy of the patient. The second axial displacement may be greater than the first axial displacement. In turn, the controller may identify the change in the tool drive parameter when the short term moving average diverges from the long term moving average by at least a differential threshold. In this approach the controller may be operative to monitor for the change in the tool drive parameter when the leading edge of the tool portion decelerates in three consecutive instances of the given amount of axial displacement of the leading edge of the tool portion. This may include monitoring an average acceleration over three consecutive intervals (e.g., with respect to time or axial displacement) to determine whether, on average the tool is decelerating over the intervals. The controller may also be operative to determine the deceleration in the leading edge based on the displacement signal by calculating the second derivative of the displacement signal.

A second aspect includes a method for use with a powered surgical instrument for sensing a position of a leading edge of a tool relative to anatomic structures of a patient. The method includes measuring a tool drive parameter that is characteristic of the tool portion acting on the patient as the tool is advanced relative to anatomical structures of the patient at a first sensor of the powered surgical instrument and outputting a tool drive signal representative of the tool drive parameter. The method includes measuring at a displacement sensor of the powered surgical instrument an axial displacement of the leading edge of the tool relative to a reference point and outputting a displacement signal representative of the axial displacement. The method also includes monitoring the tool drive signal and the displacement signal as the leading edge of the tool is advanced relative to the anatomical structures of the patient. In turn, the method includes identifying a change in the tool drive parameter over a given amount of axial displacement of the leading edge of the tool that is indicative of the leading edge of the tool moving through an interface between anatomic structures of the patient.

A number of feature refinements and additional features are applicable to the second aspect. These feature refinements and additional features may be used individually or in any combination. As such, each of the following features that will be discussed may be, but are not required to be, used with any other feature or combination of features of the second aspect.

For instance, in an embodiment, the method may include filtering the tool drive signal relative to the given amount of axial displacement of the leading edge of the tool such that changes in the tool drive parameter over distances less than the given amount of axial displacement are not identified as indicative of the leading edge of the tool moving through the interface between anatomic structures of the patient. Additionally or alternatively, the method may include determining a moving average of the tool drive parameter with respect to the axial displacement of the leading edge of the tool relative to the anatomical structures of the patient. In this latter regard, the identifying may include identifying an inflection in the moving average. In this regard and as described above, the interface may be from a medullary layer of a bone to a cortex layer of the bone, and the moving average may include a corresponding inflection from a minimum of the moving average over the given amount of axial displacement of the leading edge of the tool. Alternatively, the interface may be from a cortex layer of a bone to an exterior of the bone, and the moving average may include a corresponding inflection from a maximum of the moving average over the given amount of axial displacement of the leading edge of the tool.

In an embodiment, upon identifying the change in the tool drive parameter that indicates placement of the tool portion in a desired location, a number of actions may be taken (e.g., by the controller of the instrument). For instance, the method may include stopping operation of a drive motor of the powered surgical instrument in response to the identifying. Additionally or alternatively, the method may include alerting a user and/or measuring a displacement associated with the placement of the tool portion.

DETAILED DESCRIPTION

The following description is not intended to limit the invention to the forms disclosed herein. Consequently, variations and modifications commensurate with the following teachings, skill and knowledge of the relevant art, are within the scope of the present invention. The embodiments described herein are further intended to explain modes known of practicing the invention and to enable others skilled in the art to utilize the invention in such, or other embodiments and with various modifications required by the particular applications(s) or use(s) of the present invention.

Figure 1:
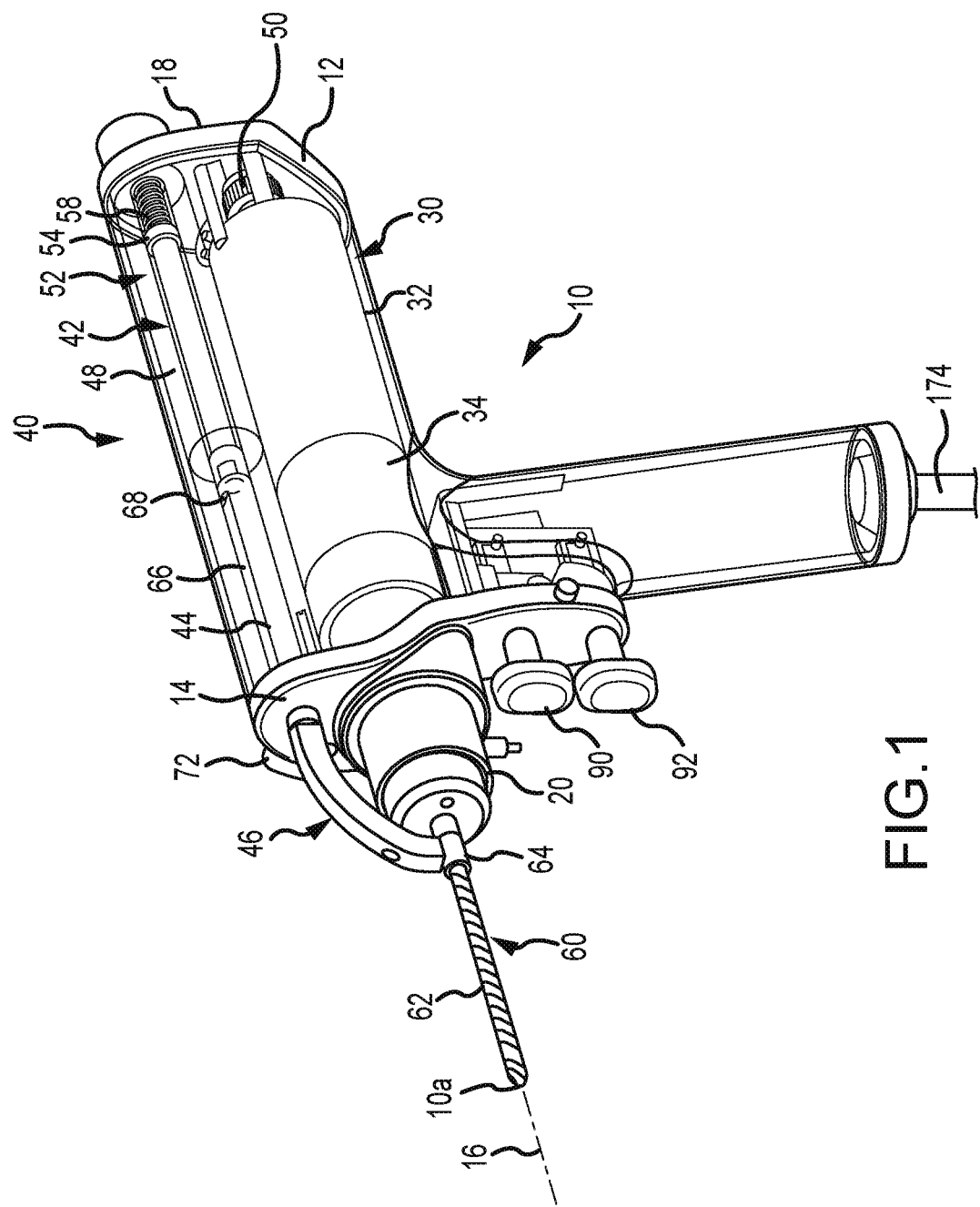
FIG. 1 is a perspective view of an embodiment of an instrument having a measurement system with a front wall of a housing not shown to provide illustration of various components within the housing.
Figure 2:
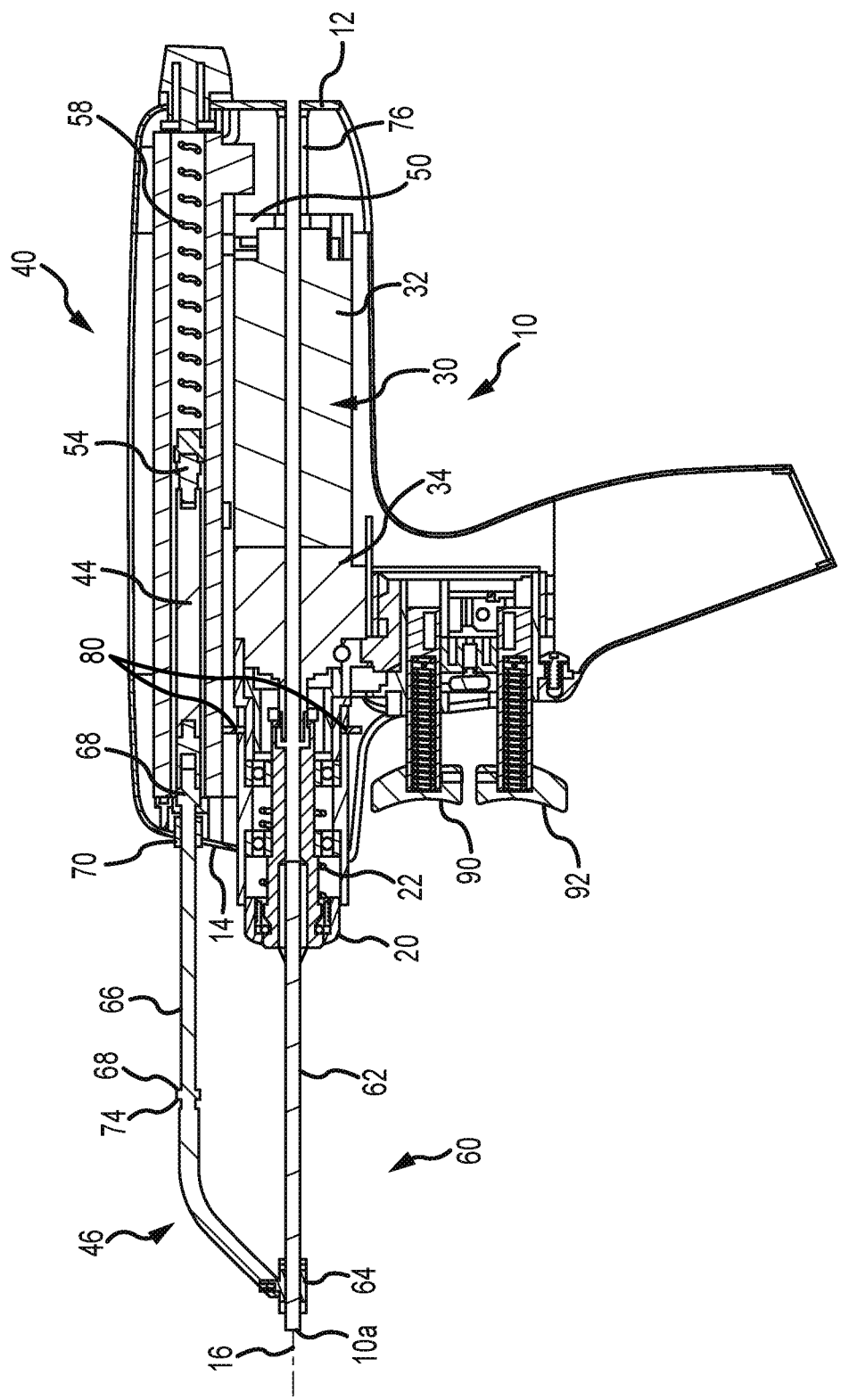
FIGS. 2 and 3 are side cut-away views of the instrument shown in FIG. 1 taken down a center portion of the instrument.
Figure 3:
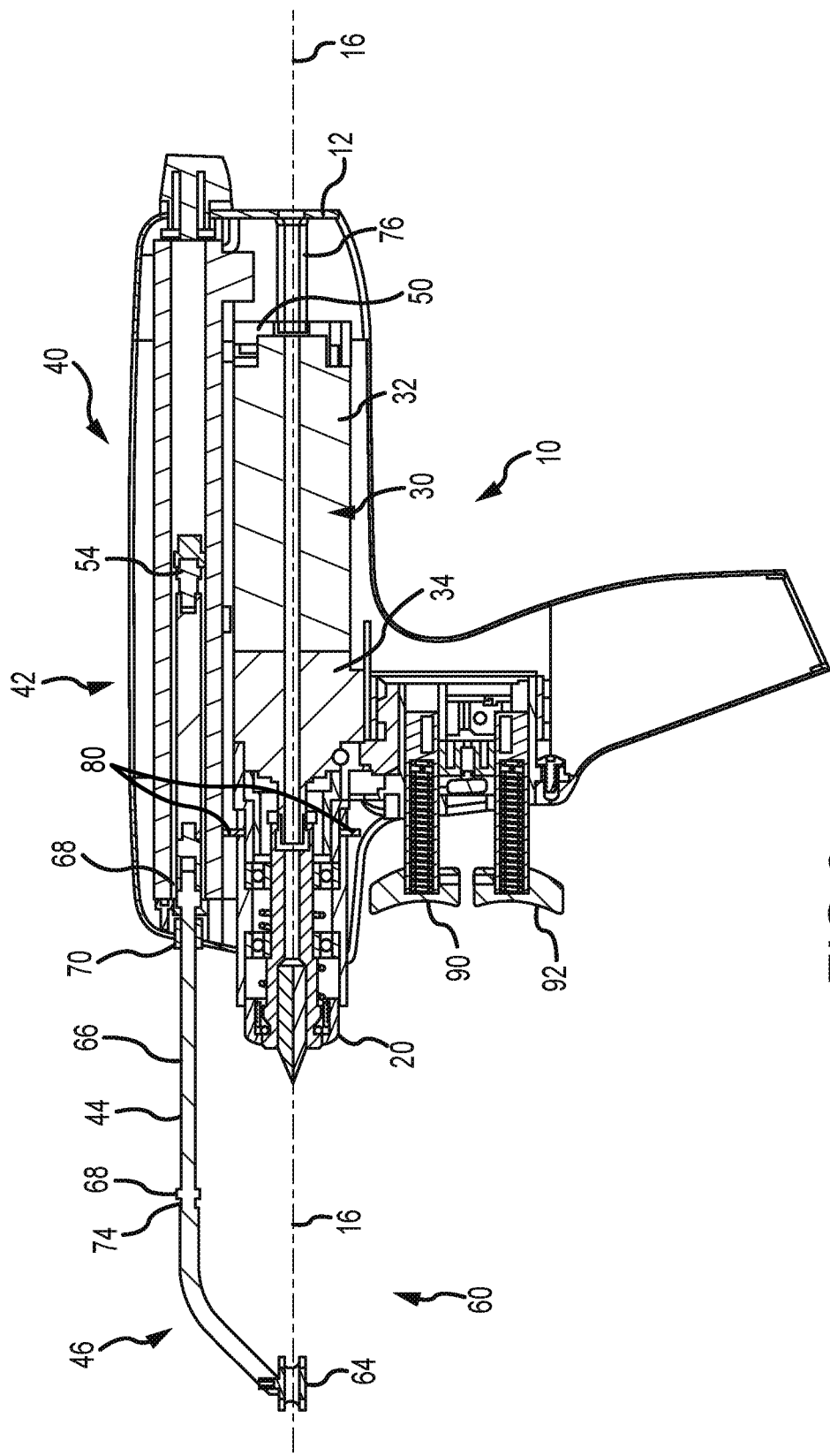

As described above, the present disclosure includes details that relates to the use of a powered surgical instrument having a measurement system for determining the placement of a tool portion of the powered surgical instrument relative to anatomy (e.g., a bone) of a patient. For instance, in various embodiments the tool portion may comprise a drill bit, a saw blade, a grinding tool, or other tool portion used for surgical operations. In other embodiments, the tool portion may include a pin or wire that is placed in the bone of the patient using a powered instrument such as a drill or the like. FIGS. 1-3 depict an embodiment of a powered surgical instrument 10 that may be utilized for such placement of a tool portion 62. As used herein, the powered surgical instrument 10 may alternatively be referred to as the powered instrument 10 and/or the instrument 10. Moreover, the tool portion 62 may be alternatively referred to as the tool 62.

As may be appreciated, tool portions 62 used in conjunction with a powered surgical instrument 10 may be used in a wide variety of surgical applications. For instance, drill bits may be used to bore holes in the anatomy of a patient, including bones. Furthermore, saws or grinders may also be utilized in orthopedic or other types of procedures. Further still, the use of implants such as pins (e.g., IM pins) and/or wires (e.g., K-wires) may be used in a variety of surgical applications, especially in the field of orthopedic surgery. The implants may be used to provide traction to the bones of a patient. Moreover, the implant may be placed to allow for induced motion of a bone (e.g., to provide alignment, rotation, or other manipulation of a bone). Furthermore, orthopedic implants may be used for fixation to secure fractured bone portions. In any regard, for the various embodiments and contexts of uses for the tool portions 62 contemplated herein, different relative placements may be desired. Such placement may be aided when using a powered surgical instrument 10 by use of a measurement system 40 that may assist in determining placement of the tool portion 62 as described in detail below.

As will be described in greater detail below, use of a powered instrument 10 having a measurement system 40 may provide a number of benefits in relation to placement of a tool portion 62. For instance, because the measurement system 40 may have the capability of automatically detecting when a tool 62 passes through a particular portion of anatomy, the user of the instrument may not be required to determine placement of the tool 62 by "feel" alone. In turn, the time required to place a tool 62 may be reduced. Moreover, the repeatability and/or reliability of tool 62 placement may be increased. Specifically, the present disclosure relates to improved systems and methods that allow for more accurate reliable tool 62 placement. Such reliability may be provided by various filtering and/or signal processing approaches taken by a computerized controller of the measurement system 40 that will be described in greater detail below.

The instrument 10 may include a chuck 20 for engagement of the tool portion 62. The tool portion 62 may comprise a tool assembly 60 that may be specifically adapted for utilization with the measurement system 40 of the instrument 10. For instance, the assembly 60 may include the tool portion 62 and a correspondingly sized bushing 64 as will be described in greater detail below.

A drive system 30 may be provided that may include a motor 32. In at least some embodiments, the drive system 30 may also include a gearbox 34. In turn, the drive system 30 may engage the chuck 20 to impart rotational motion to the chuck 20 about a working axis 16. In other embodiments, vibratory or oscillating motions (e.g., in the case of a saw or the like) may be created such that a tool engagement portion imparts an appropriate movement to the tool portion 62. In such contexts, the working axis 16 may be an axis along which the tool portion 62 is advanced, where the motion of the tool may be along or orthogonal to the working axis 16. In embodiments in which the motion imparted by the drive system 30 is rotary, the working axis 16 may define an axis of rotation about which the drive system 30 may induce rotation of the chuck 20 and, when engaged therewith, a tool portion 62.

In any regard, the tool portion 62 may be advanced along the working axis 16. Notably, the chuck 20 and drive system 30 may be cannulated to accept a tool portion 62 corresponding to a pin or wire as described above. Furthermore, the drill housing 12 may also be cannulated such that a tool portion 62 may pass entirely through the body the instrument 10 including the chuck 20, drive system 30, and housing 12. In this regard, the instrument 10 may include a cannulated passage 76 that may extend from the proximal portion of the instrument 10 to a distal portion thereof. This cannulated passage may be defined, at least in part, by the chuck 20, the drive system 30, and/or the housing 12. As such, the chuck 20 may also include a cannulated passage 22. In this regard and as will be described in greater detail below, the cannulated passage 22 of the chuck 20 may be selectively aligned to the cannulated passage 76 of the instrument 10 in embodiments where the chuck 20 selectively removable from the instrument 10 for interchanging of the chuck utilized with the instrument 10.

With continued reference to FIGS. 1-3, an embodiment of a measurement system 40 is shown. The instrument 10 may be adapted for use with a tool assembly 60 that may include a bushing 64. The bushing 64 may be correspondingly sized to extend about at least a portion of the tool portion 62 to allow for constrained axial movement of the bushing 64 relative to the tool portion 62. Alternatively, the bushing 64 may be integrally provided with the measurement system 40 as described in greater detail below. The instrument 10 may comprise at least some components of the measurement system 40 within the housing 12 to facilitate operation of the measurement system 40 in connection with the instrument 10. For example, at least a portion of a displacement sensor 42 may be integrated into a housing 12 of the instrument 10. In this regard, the displacement sensor 42 may include a depth sensing arm 44 that is specifically adapted for engagement with the bushing 64 of the tool assembly 60 that may be engaged by a chuck 20 or other engagement portion of the instrument 10. While the bushing 64 is shown as a discrete part, the bushing 64 may also be provided integrally with the displacement sensing arm 44.

The measurement system 40 may also include a force sensor 50. The force sensor 50 may be disposed relative to the drive system 30. The chuck 20 and drive system 30 may contact the force sensor 50 such that the force sensor 50 is capable of measuring an axial force acting on the tool portion 62 along the working axis 16. In this regard, the chuck 20 and drive system 30 may be axially rigid such that an axial force acting on the chuck 20 (e.g., as imparted to the implant 62 upon axial advancement of the tool portion 62 engaged with the chuck 20) may be passed to the chuck 20 and drive system 30 such that the drive system 30 may impinge on the force sensor 50 such that the force sensor 50 may measure the force. Thus, the chuck 20 and drive system 30 may be supported such that the axial movement of the chuck 20 and drive system 30 is limited (e.g., to prevent error in relation to the displacement sensor 42) yet allow for the free transfer of force to the force sensor 50. That is, it is advantageous to reduce the action of errant forces on the chuck 20 and drive system 30 along the working axis 16 to improve the accuracy of the measured force at the force sensor 50. For instance, upon contact of the drive system 30 with the force sensor 50, further axial forces on the drive system 30 may result in minimal deflection (i.e., imperceptibly by the displacement sensor 40) while impinging on the force sensor 50. In this regard, the drive system 30 may be constrained for contacting engagement with the force sensor 50, but otherwise free to deflect along the working axis to achieve an accurate force measurement. In at least some embodiments, the drive system 30 may be preloaded to impart a preloaded force against the force sensor 50. In this regard, the force sensor 50 may measure a differential between the preload force and a measured force to determine an applied force to the tool portion 62.

Figure 10B:
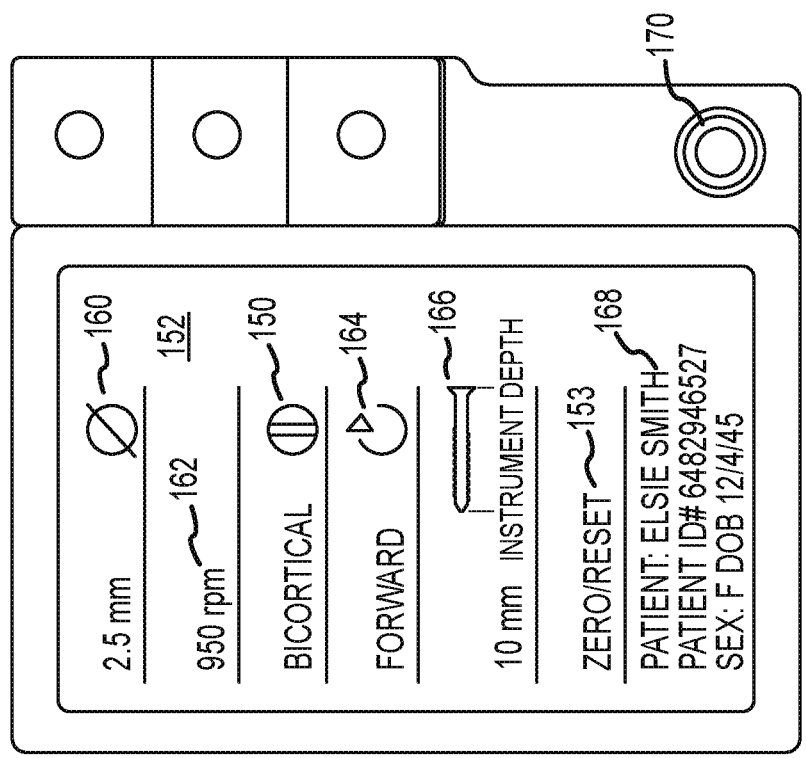
FIG. 10B depicts an embodiment of an instrument interface of the controller of FIG. 10A.
Figure 10A:
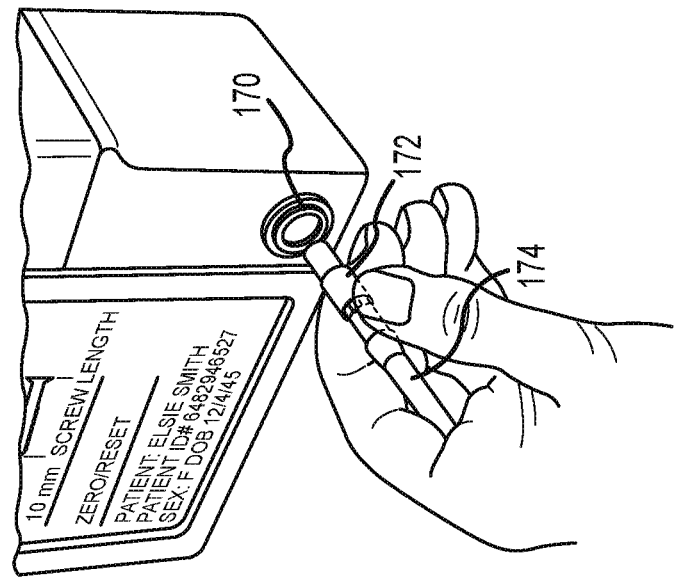
FIG. 10A depicts an embodiment of an interface of a controller.

The drive system 30, displacement sensor 42, and/or force sensor 50 may each be in operative communication with a controller 146. The controller 146 may be a computerized controller that may include a processor and memory that stores instructions executable by the processor to perform signal analysis of the outputs of the displacement sensor 42 and/or force sensor 50. Furthermore, the controller 146 may be in control of the drive system 30 (e.g., to control the operation and/or cessation of operation of the drive system 30). As shown in FIGS. 10A and 10B, the controller 146 may comprise a remote unit to which the instrument is operatively coupled for communication therewith. Alternatively, the controller 146 may be integrated into the housing 12 of the instrument 10. The operation of the controller 146 in relation to the instrument 10 is described in greater detail below.

Returning to the description of the displacement sensor 42, the depth sensing arm 44 may be used to establish a reference point from which displacement of a tool portion 62 may be measured. In this regard, as follows herein, a general description of the features and operation of the instrument 10 used in conjunction with the tool assembly 60 is provided.

The depth sensing arm 44 may extend from the drill housing 12. For example, the depth sensing arm 44 may extend distally (e.g., from a distal face 14 of the drill housing 12) in a direction corresponding with the direction in which the tool portion 62 extends from the chuck 20 of the instrument 10 for advancement relative to the anatomy of the patient. At least a portion of the displacement sensing arm 44 may extend from the drill housing 12 parallel to the working axis 16 of the instrument 10. The depth sensing arm 44 may also include a distal portion 46 that is adapted to engage the bushing 64 provided with the tool assembly 60. Alternatively, the distal portion 46 may include an integrally provided bushing 64 as described above. As used herein, distal may correspond to a direction toward the leading edge 10a of the tool portion 62 and proximal may correspond to a direction away from the leading edge 10a of the tool portion 62 toward an opposite end of the tool portion 62. In this regard, at least a portion of the depth sensing arm 44 (e.g., the distal portion 46) may be adapted to engage the bushing 64 of the tool assembly 60. In any regard, at least a portion of the depth sensing arm 44 may extend into the housing 12.

In an embodiment, the displacement sensor 40 may comprise a linear variable differential transformer (LVDT) sensor that is adapted to sense the position of a core 54 relative to a coil 48. Accordingly, the housing 12 may contain a coil 48. A proximal end 52 of the displacement sensing arm 44 may include the core 54 that may interact with the coil 48 of the displacement sensor 40. Specifically, as shown in FIG. 1, the depth sensing arm 44 is in a retracted position relative to the tool portion 62. For example, this retracted position shown in FIG. 1 may occur when the tool portion 62 is advanced during placement of the tool portion 62 relative to the anatomy of a patient (e.g., such that the portion of the tool portion 62 extending beyond the distal edge of the bushing 64 would be disposed in the anatomy of the patient such as a bone or the like). In this regard, the proximal end 52 of the displacement sensing arm 44 may be disposed within the coil 48 of the displacement sensor 40. Accordingly, as the proximal end 52 of the displacement sensing arm 44 is moved relative to the coil 48, the location of the core 54 may be determined relative to the coil 48 (e.g., by monitoring the induced current of the coil 48) to provide an output that is indicative of the position of the core 54, and in turn the position of the displacement sensing arm 44 relative to the drill housing 12. That is, the depth sensing arm 44 may be displaceable relative to the coil 48 such that the displacement sensor 42 may be operable to sense a change in position of the depth sensing arm 44 and output a measure of the displacement that may be used in determining a depth of penetration of the tool portion 62 relative to the anatomy the tool portion 62 is advanced. In an embodiment, the total measurable travel of the core 54 relative to the coil 48 may be at least about 2.5 in (6.4 cm). Furthermore, the resolution of the output of the displacement sensor 42 may be about 0.1% (e.g., about 0.002 inches (0.06 mm) for a sensor having a total measurable travel of 2.5 inches (6.4 cm)).

While a LVDT displacement sensor is shown and described in relation to the instrument 10 shown in the accompanying figures, it may be appreciated that other types of displacement sensors may be provided. For instance, the sensor may provide for the absolute or relative measurement of the position of the distal end 46 of the displacement sensing arm 44 to provide a displacement measure. For instance, in another embodiment, an optical displacement sensor may be provided. Other types of displacement sensors are also contemplated such as, for example, a capacitive displacement sensor, ultrasonic sensors, Hall effect sensors, rotary encoders, linear encoders, or any other sensors known in the art capable of outputting an absolute or relative position measure. In any regard, the use of the bushing 64 that is engaged with the displacement sensing arm 44 may allow for a reference point to be established using the bushing 64 resting external to the substrate into which the tool portion 62 is advanced. For instance, the controller 146 may receive an input to reset or "zero" the measure of the displacement sensor 42 when the bushing and leading edge 10a of the tool portion 62 are in contact with a reference (e.g., an exterior portion of a bone) into which the tool portion 62 is to be advanced. Accordingly, any relative movement of the tool portion 62 relative to the bushing 64 may be measured by the controller 146 to determine the depth of penetration of the leading edge 10a of the tool portion 62 as it is advanced into the anatomy of the patient (e.g., a patient's bone).

A biasing member 58 (e.g., a coil spring) may be provided relative to the proximal end 52 of the displacement sensing arm 44. In this regard, the biasing member 58 may act on the proximal end 52 of the displacement sensing arm 44 to bias the displacement sensing arm 44 distally. This may assist in maintaining the bushing 64 in contact with the bone to increase the accuracy of the displacement sensor 42.

In an embodiment, the displacement sensing arm 44 may include features that selectively prevent ejection of the displacement sensing arm 44 from the instrument in the distal direction when the displacement sensing arm 44 is distally biased. For example, the displacement sensing arm 44 may include at least one flat portion 66 that extends along a portion of the displacement sensing arm 44. At the proximal and distal extents of the flat 66, the displacement sensing arm 44 may include shoulders 68 that project from the flat 66. As such, a selectively displaceable stop 70 (best seen in FIGS. 2 and 3) may be disposed relative to the flat portion 66 such that the flat portion 66 may move distally and proximally relative to the stop 70. However, the stop 70 may interfere with the shoulder 68 defined in the displacement sensing arm 44 to prevent passage of the shoulders 68 beyond the stop 70. That is, a distal shoulder 68 may limit proximal movement of the displacement sensing arm 44 beyond the stop and a proximal shoulder 68 may limit distal movement of the displacement sensing arm 44 beyond the stop 70. In this regard, the length of the displacement sensing arm 44 along which the flat portion 66 extends may be moveable relative to the stop 70 between the distal and proximal shoulders 68 defined at the ends of the flat portion 66.

However, the stop 70 may be displaceable by, for example, depressing a button 72 provided on an exterior of the housing 12. Thus, upon depressing the button 72, the stop 70 may be displaced away from the displacement sensing arm 44 to allow the shoulder 68 to pass by the stop 70 such that the displacement sensing arm 44 may be removed from the instrument 10. Additionally, the distal end of the flat 66 may include a detent 74 that may be engageable with the stop 70 so as to maintain the displacement sensing arm 44 in a proximally disposed, retracted position relative to the housing 12 such as that shown in FIG. 1. Once the button 70 is depressed and released, the detent 74 at the proximal end of the flat portion 66 may be released by the stop 70 and the displacement sensing arm 44 may move proximally (e.g., under influence of the biasing member 58). The displacement sensing arm 44 may move proximally until the shoulder 68 at the distal end of the flat 66 are engaged to prevent further distal movement of the displacement sensing arm 44. Accordingly, the displacement sensing arm 44 may be retained in a retracted position (e.g., for improved visibility of the distal end of the tool portion 62 or to stow the displacement sensing arm 44 when not in use). However, the displacement sensing arm 44 may be released to be moveable relative to the housing 12. Moreover, the displacement sensing arm 44 may be removable altogether from the housing 12.

In the latter regard, removal of the displacement sensing arm 44 and biasing member 58 from the instrument 10 may allow for separate cleaning (e.g., in an autoclave) of those members. Additionally, removal of the displacement sensing arm 44 may allow for a cleaning apparatus (e.g., a brush or the like) to be passed through the instrument 10 to facilitate cleaning thereof.

As referenced above, in an embodiment the distal portion 46 of the displacement sensing arm 44 may be adapted to engage the tool assembly 60 (e.g., a bushing 64 thereof) that is correspondingly adapted for use with the instrument 10. In this regard, the tool assembly 60 may include the tool portion 62 and the bushing 64. The bushing 64 may be adapted for movement along the tool portion 62 relative to the working axis of the tool portion 62. The displacement sensing arm 44 may engage the bushing 64 such that movement of the bushing 64 relative to the tool portion 62 may also cause relative movement of the displacement sensing arm 44 relative to the tool portion 62. The displacement sensing arm 44 may generally be linear along a proximal portion 52 of the displacement sensing arm 44. In this regard, the proximal portion 52 may be adapted to be parallel with the cannulated passage 76 that extends along the working axis 16.

Furthermore, the distal portion 46 of the displacement sensing arm 44 (e.g., the portion distal to the linear portion of the displacement sensing arm 44) may extend from the linear portion of the displacement sensing arm 44 toward the tool assembly 60 that may be engaged by the chuck 20 of the instrument 10. In this regard, the linear portion of the displacement sensing arm 44 may be substantially parallel to and offset from the working axis 16. The distal portion 46 may extend from the linear portion in a direction corresponding with the offset such that the distal portion 46 extends toward the tool assembly 60. This may facilitate engagement between the displacement sensing arm 44 and the bushing 64 of the tool assembly 60 (e.g., using a post and hole as described in U.S. Pat. No. 9,370,372, which is incorporated by reference herein in its entirety).

The distal portion 46 may be an at least partially arcuate member extending along a radius of curvature toward the tool assembly 60. However, the distal portion 46 may be shaped differently (e.g., the distal portion 46 may be a linear portion extending at an angle or perpendicularly from the proximal portion 52 toward the tool assembly 60). The configuration and operation of the measurement system 40 of the instrument 10 may be as described in any of the embodiments in U.S. Pat. Nos. 6,665,948, 9,370,372, or U.S. Patent Pub. No. 2016/0128704, all of which are incorporate by reference herein in their entireties. Moreover, operation of the bushing 64 in relation to the displacement sensing arm 44 may be according to any of the foregoing documents incorporated by reference. In this regard, the bushing 64 may interact with the tool portion 62 in a manner similar to that described in relation to the bushing interacting with the drill bit or other instrument tool portion 62 described in the foregoing documents incorporate by reference.

Figure 4:
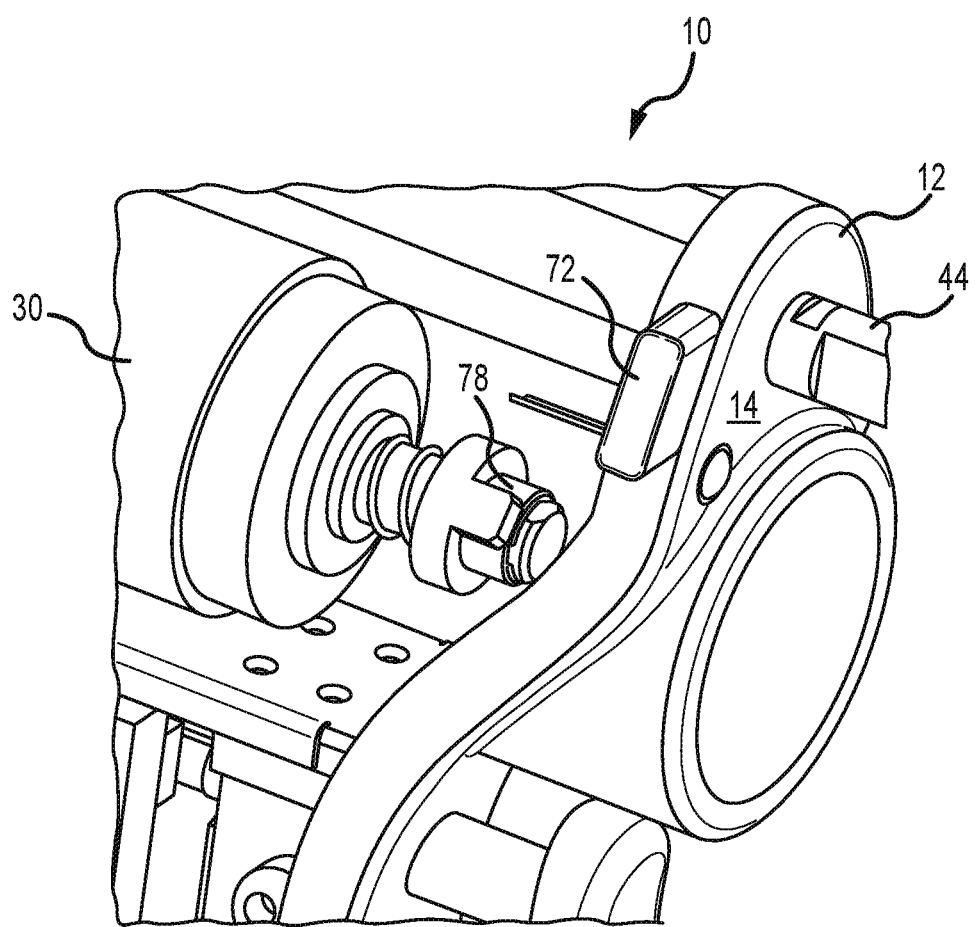
FIG. 4 is a perspective view of an embodiment of a chuck engagement portion of an instrument with a portion of the instrument housing hidden to provide illustration of the chuck engagement portion.

As described briefly above, the chuck 20 may be selectively engageable and disengageable with the instrument 10. In this regard, various different chucks may be selectively utilized in conjunction with the instrument 10. To facilitate the different chucks, the instrument 10 may provide a standardized chuck engagement format to engage the various different potential embodiments of chucks 20 that may be utilized with the instrument 10. In this regard, as may be appreciated in FIG. 4, the instrument 10 may include a corresponding chuck drive coupling 78 that engages with a chuck 20 to impart rotational motion from the drive system 30 to the chuck 20. In this regard, the chuck 20 may be detachable from the drill 50. The chuck drive coupling 78 may be in operative communication with the drive system 30 such that the drive system 30 rotates the drive coupling 78. In turn, the chuck drive coupling 78 may engage with the chuck 20 to rotate at least a portion thereof. Furthermore, any chuck 20 configured for engagement with the instrument 10 may include a cannulated passage 22 that is alignable with the cannulated passage 76 of the instrument when the chuck 20 is engaged therewith.

Figure 5:
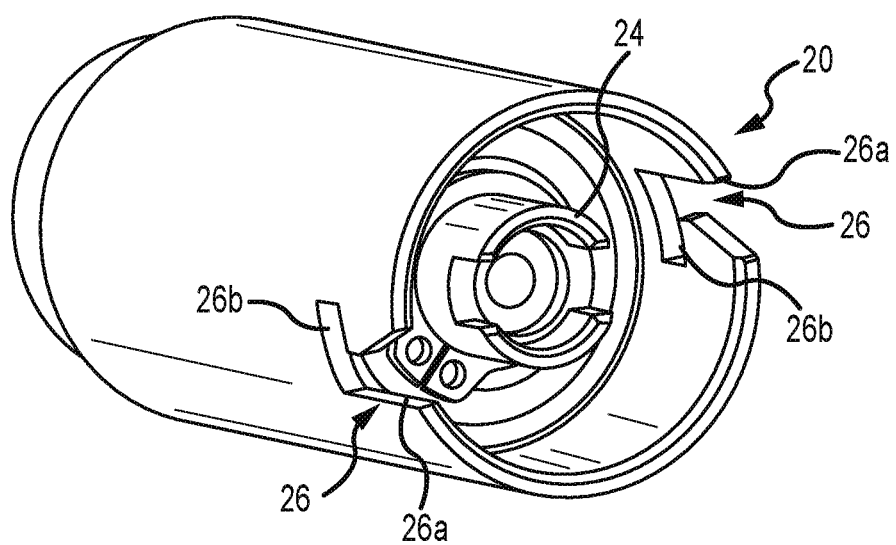
FIG. 5 is a perspective view of an embodiment of a chuck.

With further reference to FIG. 5, the proximal end of the chuck 20 may include a chuck drive shaft 24 disposed relative to slots 26. The slots 26 may coordinate with corresponding tabs 80 provided with the instrument 10 adjacent to the chuck drive coupling 78 (best seen in FIGS. 2 and 3) to retain the chuck 20 relative to the instrument 10. For instance, the tabs 80 may be rigidly engaged with the drive system 30. In turn, the chuck drive shaft 24 may be keyed or otherwise configured such that the chuck shaft 24 engages the chuck drive coupling 78 of the instrument 10. In turn, the chuck drive coupling 78 may impart rotational motion to the chuck drive shaft 24 to rotate a tool portion 62 engaged with the chuck 20. The slots 26 may coordinate with the tabs 80 so as to allow the chuck 20 to be quickly attached and/or released from the instrument 10 by engagement of the slots 26 with the tabs 80. This may be appreciated from FIG. 5, where it is illustrated that the slots 26 may include a first portion 26a that extends parallel to the working axis 16.

The chuck may be advanced toward the chuck drive coupling 78 along the working axis 16 such that the tabs 80 travel along the first portion 26a to the distal end thereof. The slots 26 may also include a second portion 26b that extend circumferentially about the chuck 20. As such, once the tabs 80 abut the distal end of the first portion 26a, rotation of the chuck 20 may move the second portion 26b such that the tabs 80 extend into the second portion 26b, thus restricting the chuck 20 from movement relative to the working axis 16. That is, when the tabs 80 are disposed in the second portion 26b, the second portion 26b may be sized as to engage the tabs 80 to limit axial movement of the chuck 20 relative to the working axis 16 (e.g., to allow the chuck 20 to travel relative to the force sensor 50 for transferring force thereto, but to disallow the chuck 20 from moving distally from the instrument 10). Further locking mechanisms may be provided to prevent the chuck 20 from rotating relative to the working axis 16 when engaged so that the tabs 80 do not slip from the second portion 26*b*. For example, a release may be provided to lockingly maintain the chuck 20 in position to the instrument 10 such that the chuck 20 is only released for removal upon actuation of the release. Thus, the chuck 20 may be quickly and efficiently attached and detached from the instrument 10.

In this regard, when the chuck 20 is engaged with the drive system 30, the tool portion 62, chuck 20, and drive system 30 may define an axially rigid structure that may transmit a force acting axially on the tool portion 62 along the working axis 16 along the rigid structure such that the force sensor 50 is operative to detect the force acting on the tool portion 62. As is discussed in greater detail below, a controller of the instrument 10 may be operative to monitor one or more parameters of the instrument 10 to determine placement of the tool portion 62.

With further reference to FIGS. 10A and 10B, an embodiment of a controller 146 is shown that may be utilized with the instrument 10. Specifically, as described above, the instrument 10 may have a displacement sensor 42 for outputting a signal indicative of the relative displacement of a tool portion 62 (e.g., a leading edge 10*a* of the tool portion 62). Also, the instrument 10 may have a force sensor 50 for measurement of the force acting on the tool portion 62 axially along the working axis 16. In other embodiments, additional or alternative sensors may be provided for generating tool drive signals representative of a tool drive parameter that is characteristic of the operation of the tool portion 62. The instrument 10 may include a telemetry cable 174 in operative communication with the displacement sensor 42 and the force sensor 50. The telemetry cable 174 may have a connector 172 that may interface with a data port 170 of the controller 146. While a telemetry cable 174 is shown for interfacing with the controller 146, other approaches are possible for relay of data from the instrument 10 to a controller 146 such as, for example, by way of wireless telemetry via a wireless protocol such as Bluetooth, IEEE 802.11, or the like. Furthermore, the controller 146 may not be a separate unit, but may be integrated into the instrument 10 as described above.

As depicted, the controller 146 may include a touchscreen interface 152 for use by a user to interface with the controller 146. The interface 146 may allow a user to set a diameter or other characteristic of the working tool 62 at a selection portion 160. Moreover, the rotational speed of the instrument may be displayed and/or controlled at the speed selection 162. An operation mode may be selected or input at the mode selection 150 as will be described in greater detail below. Also, the instrument direction may be selected or input at the direction selection 164. In an embodiment, the instrument 10 may measure a depth of a bore. This may be output in the length measurement output 166. Also, the controller 146 may have a reset selection 153 to allow for resetting the instrument (e.g., for establishing a reference point for the displacement sensor 42 and/or calibrating the force sensor 50). While a reset selection 153 may be provided on the controller 146, the reset selection 153 may be triggered by use of a first trigger 90 and a second trigger 92 of the instrument 10. For instance, in normal operation, actuation of the first trigger 90 may result in operation of the instrument 10 in a first direction (e.g., clockwise relative to the working axis 16). Actuation of the second trigger 92 may result in operation of the instrument 10 in an opposite direction (e.g., anticlockwise relative to the working axis 16). Actuation of the first trigger 90 at the same time as the second trigger 92 may send a reset signal to the controller 146 to zero a depth measurement (e.g., to establish a reference point). Actuation of the first trigger 90 simultaneously with the second trigger 92 may also sequence the controller 146 (e.g., to indicate a new task or tool portion 62 is to be utilized). The controller 146 may also display administrative data 168 (e.g., regarding an operation, patient, instrument status information, etc.).

Figure 6:
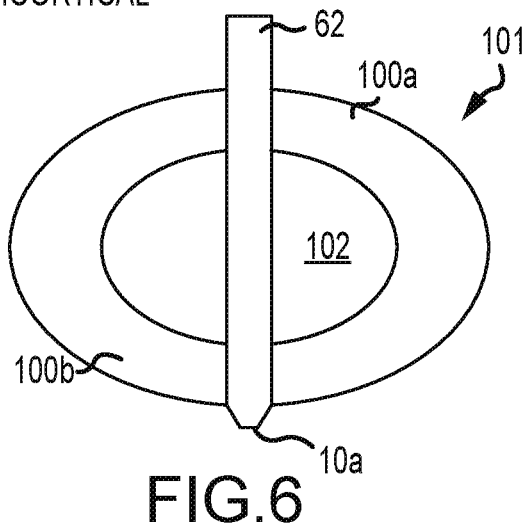
FIG. 6 is a schematic representation of bicortical placement of a tool portion relative to a bone of a patient.

In relation to the mode selection 150, the controller 146 may be configured to perform in various different modes using the mode selection 150. As an example, the different modes of operation may correspond with different relative placements of the leading edge 10*a* of the tool portion 62 relative to the anatomy of a patient. Different placements of an orthopedic implant are depicted in FIGS. 6, 7, 8, and 9. For instance, a bicortical bone cross-section such as those depicted in FIGS. 6-9 may include a hard outer cortex that surrounds a medullary layer 102. In this regard, in bicortical operation is depicted in FIG. 6, the leading edge 10*a* of the tool portion 62 may be advanced through a first portion of the hard outer cortex 100*a*, the medullary layer 102, and a second portion of the hard outer cortex 100*b*. In turn, when the leading edge 10*a* breaches the exterior of the second portion of the hard outer cortex 100*b*, the instrument 100 may be arrested such that the tool portion 62 is placed as depicted in FIG. 6 where the leading edge 10*a* just breaches the entire bicortical length of the bone. Bicortical operation of the instrument 10 is generally described in U.S. Pat. No. 6,665,948 which is incorporated by reference herein.

Figure 7:
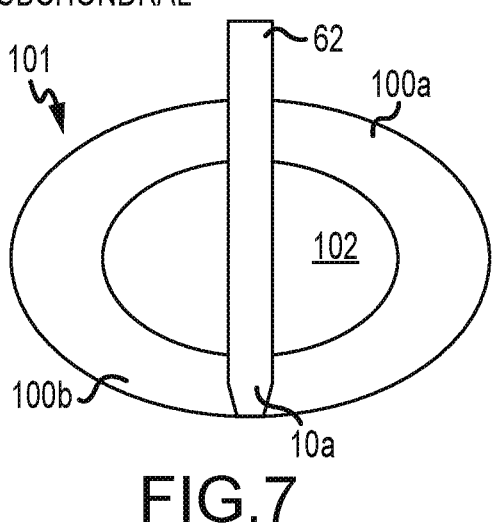
FIG. 7 is a schematic representation of subchondral placement of a tool portion relative to a bone of a patient.

FIG. 7 depicts another mode of operation corresponding to subchondral placement of the tool portion 62. In this regard, the leading edge 10*a* of the tool portion 62 is advanced through the first portion of hard outer cortex 100*a*, the medullary layer 102, and a portion of the second portion of hard outer cortex 100*b*. In this regard, the instrument 10 may be arrested when the leading edge 10*a* is embedded in the second portion of hard outer cortex 100*b* as shown in FIG. 7.

Figure 8:
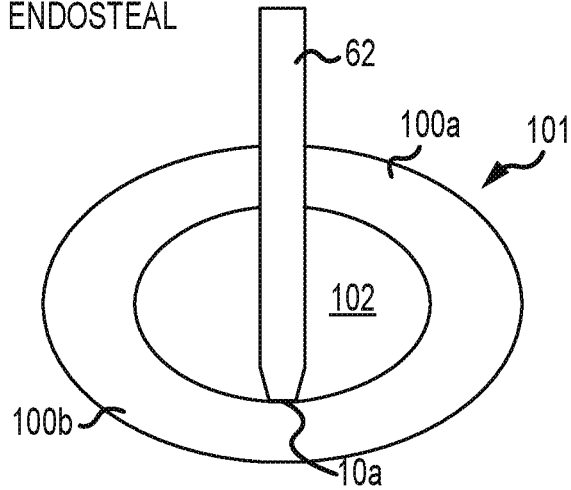
FIG. 8 is a schematic representation of endosteal placement of a tool portion relative to a bone of a patient.

FIG. 8 depicts another mode of operation corresponding to an endosteal placement of the tool portion 62. In this regard, the leading edge 10*a* may be advanced through the first portion of hard outer cortex 100*a* and through the medullary layer 102. The instrument 10 may be arrested when the leading edge 10*a* reaches the second portion of hard outer cortex 100*b* such that the leading edge 10*a* is disposed at the interface of the medullary layer 102 and the second portion of hard outer cortex 100*b*.

Figure 9:
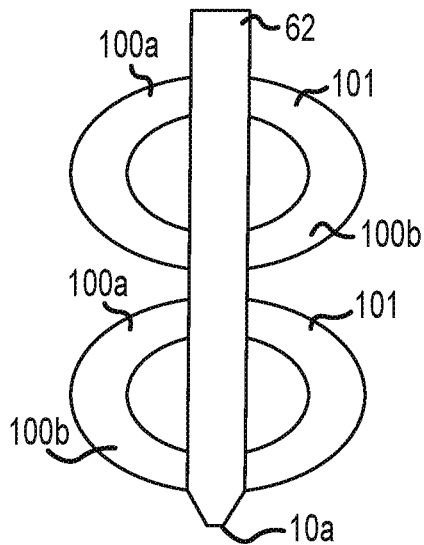
FIG. 9 is a schematic representation of multicortical placement of a tool portion relative to a bone of a patient.

FIG. 9 depicts another mode of operation corresponding to multi-cortical placement of the tool portion 62. In this mode, the leading edge 10*a* of the tool portion 62 is advanced through a plurality of bones 101. In this regard, the number of bones through which the tool portion 62 is to be advanced may be set such that instrument 10 is arrested when the leading edge 10*a* of the tool portion 62 breaches the second portion of hard outer cortex 100*b* of the last bone 101 through which the tool portion 62 is to be advanced. Multi-cortical placement of the implant 62 may involve setting occurrence flags that may at least in part be based on the number of bones though which the tool portion 62 is to pass. For instance, if two bones are to be drilled through, the fourth occurrence of the passing of the leading edge 10*a* from a first medium into a second medium having a lower density may indicate completion of the operation. Also, while a bicortical placement is shown in FIG. 9, the multi-cortical mode may have submodes that allow for bicortical, subchondral, or endosteal placement through multiple bones using identification techniques to place the tool portion 62 in the last bone in the series of bones through which the tool portion 62 is to be advanced. That is, the measurement system 40 may monitor penetration through n−1 bones where n is the number of the last bone in which the tool portion 62 is to be placed. For the nth bone, any of the following specific techniques may be used for bicortical, subchondral, or endosteal placement of the tool portion 62 in the last bone.

Any of the foregoing placements may correspond with modes of operation of the instrument 10. For instance, selection of a mode corresponding to any one of the foregoing placements may be utilized by selection via the mode selection 150 of the controller 146. As such, when a corresponding one of the modes is selected, the controller 146 may be operative to control operation of the measurement system 40 so as to arrest the instrument 10 when the leading edge 10a of the tool portion 62 reaches the placement designated for the mode or may output an alarm or take some other action. In this regard, any one of a variety of approaches may be utilized to determine when the tool portion 62 reaches the various placements described above. In this regard, various embodiments of methods are described herein.

For instance, determination of the position of the leading edge 10a of the tool portion 62 relative to the structure of a bone 101 may be determined by analyzing a signal output from a force sensor 50 and/or displacement sensor 42 of a measuring system 40 as described in the '948 Patent incorporated by reference in its entirety above. While a force sensor 50 is described herein, it may be appreciated that other tool drive parameters may be monitored using an appropriate sensor as described above. Thus, while a force sensor 50 is described, this is for illustrative purposes and is not limiting.

As the leading edge 10a passes through the various interfaces of the bone structure 101, these interfaces may be detected based on signals from the force sensor 50 and displacement sensor 42. For instance, when the leading edge 10a passes from the first portion of hard cortex 100a to the medullary layer 102, the tool portion 62 may experience a change in force (e.g., a decrease in the force) sensed by the force sensor 50 and an increase in acceleration. The decrease in the force may be determined by taking the derivative of the signal output from the force sensor 50. Specifically, the derivative of the signal output from the force sensor 50 may become negative, indicating a negative rate of change of the force applied. Alternatively, a local minimum of a second derivative of the force may be determined that corresponds to a reduction in the force acting on the tool portion 62. For instance, a second derivative of the force signal may be taken and the local minimum of the second derivative of the force signal may be determined using any appropriate computational approach to determine such a state in the force signal. Additionally, taking the second derivative of the output from the displacement sensor 42 may provide a signal indicative of the acceleration. This technique may also be used to determine when the tool portion 62 passes through the second portion 100b of hard cortex 100. This may be the first occurrence of a decrease in force and increase in acceleration in the case of unicortical operation or the second occurrence in the case of bicortical operation. In any regard, it may be appreciated that the change in the force may be used to detect when the tool portion 62 passes from one medium to another, whether it be an increase or a decrease in force.

Moreover, it may be determined when the leading edge 10a contacts the second portion 100b of cortex 100 after passing through the medullary layer 102. In this regard, a decrease in acceleration and an increase in force as measured from the displacement sensor 42 and the force sensor 50 may be utilized to determine the second portion 100b of cortex 100 has been contacted for endosteal placement. For subchondral placement, a given displacement offset from the contacting of the second portion 100b of the cortex 100 may be used to advance the leading edge 10a of the tool portion 62 partially into the second portion 100b of cortex 100.

Figure 11:
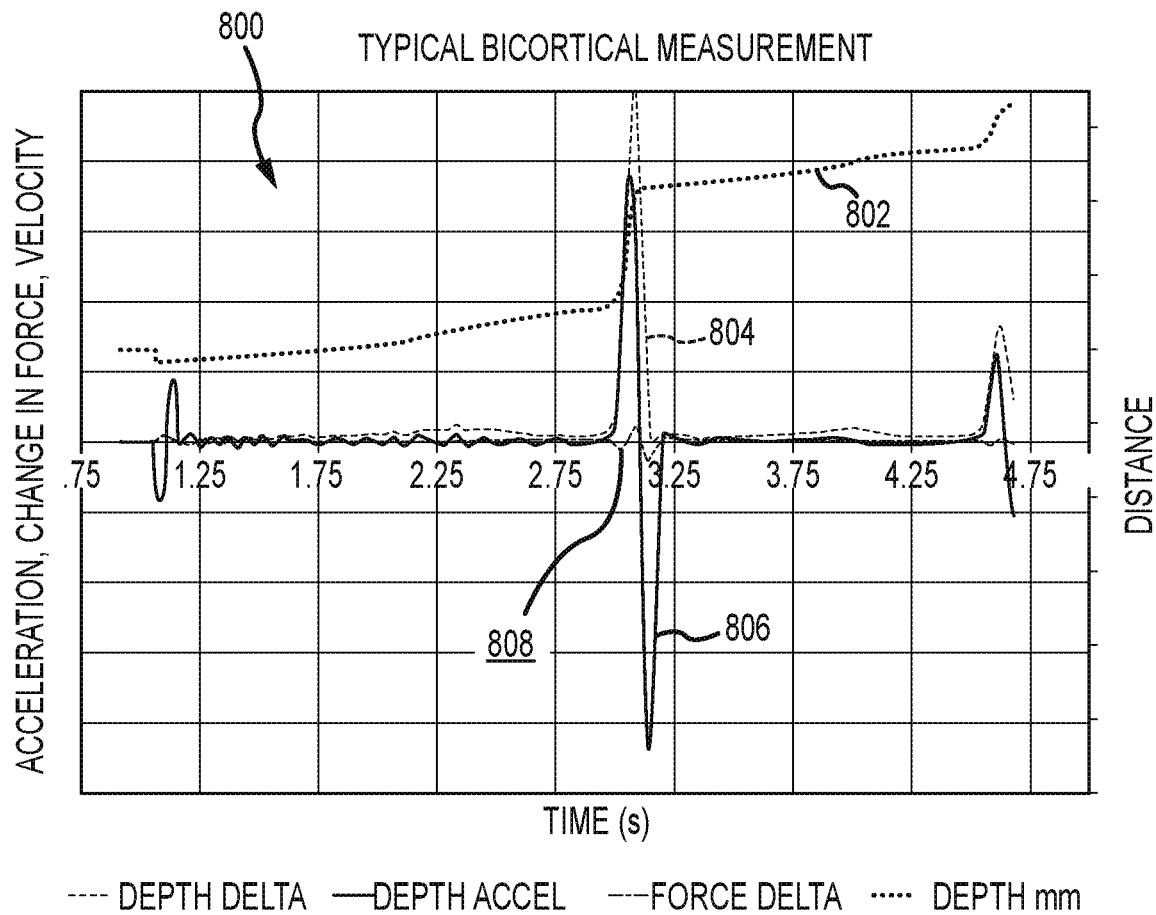
FIGS. 11 and 12 depict plots representing an embodiment of operation of the instrument.
Figure 12:
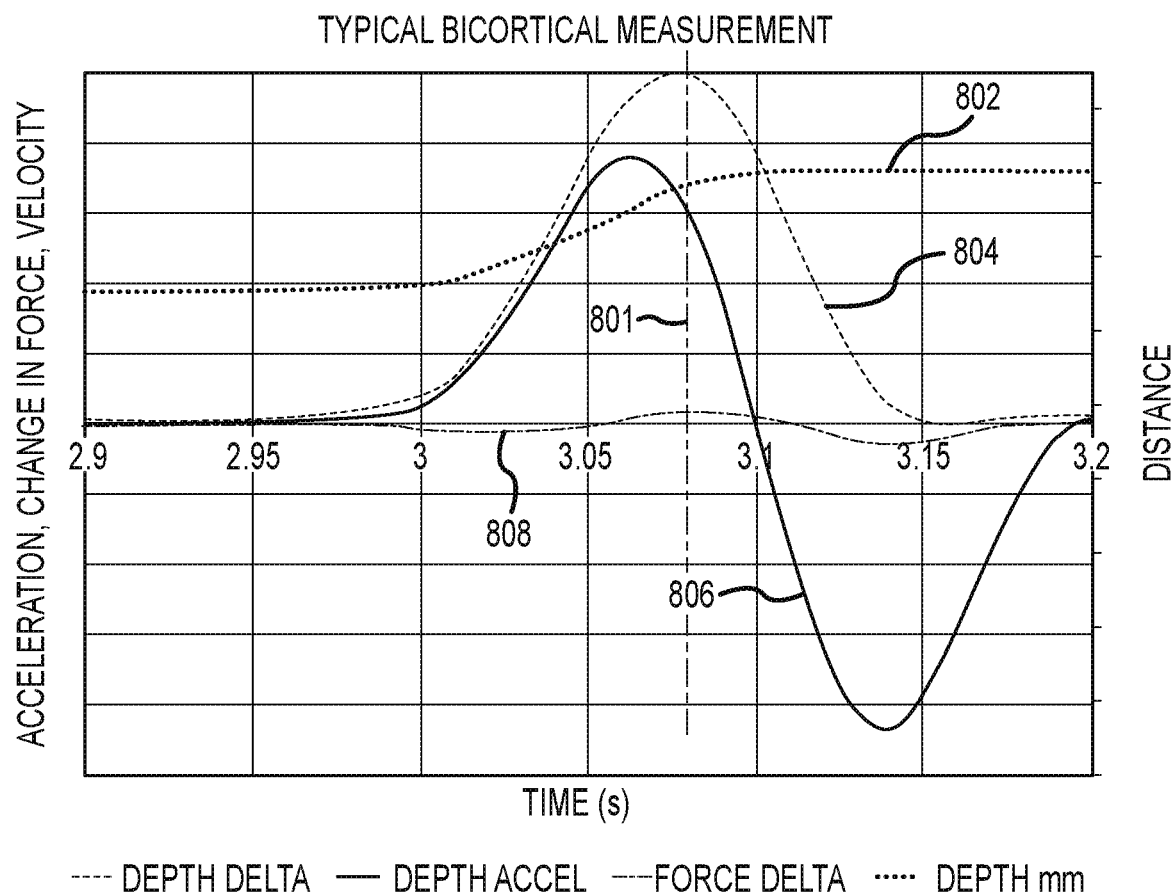

Such a context is depicted in FIGS. 11 and 12. FIG. 11 depicts a plot 800 of various sensor outputs and/or calculated signals during a normal bicortical pass of a leading edge 10a of a tool portion 62 through a bone 101 of a patient. The plot 800 includes a displacement signal 802. The displacement signal 802 may be a directly measured signal from a displacement sensor 42 of a measurement system 40. Alternatively, the displacement signal 802 may be derived from another sensor (e.g., as a second integral of a signal from an accelerometer or the like). The plot 800 also includes a velocity signal 804, which may be measured directly or derived from a displacement sensor or an accelerometer. The plot 800 also includes an acceleration signal 806. The acceleration signal 806 may be measured (e.g., using an accelerometer or the like) or may be derived from the displacement signal 802 (e.g., as a second derivative of the displacement signal 802). As discussed above, the velocity signal 804 may be derived from either the displacement signal 802 (e.g., as a first derivative thereof) or from the acceleration signal 806 (e.g., as a first integral thereof). Moreover, FIG. 11 may include a force signal 808 representative of a change in force as measured by a force sensor 50. In this regard, the force signal 808 may not depict an actual force measure, but rather a first derivative of actual force. FIG. 12 shows an enlarged portion of the plot 800 in a region of interest around the interfaces of the cortices.

As best seen in FIG. 12, the contact between the leading edge 10a and interface of the medullary layer 102 and the second portion 100b of cortex 100 occurs between 3.05 seconds and 3.1 second in the plot 800 at the interface 801. This interface 801 coincides with the point at which the force signal 808 (representing the first derivative of the measured force) experiences a maximum (as may be measured by determining when a second derivative of the measured force is positive). The interface 801 may also coincide with a reduction in the acceleration signal 806. As such, when the force signal 808 is at a local maximum that coincides with the acceleration being negative, the interface 801 may be determined.

Figure 13:
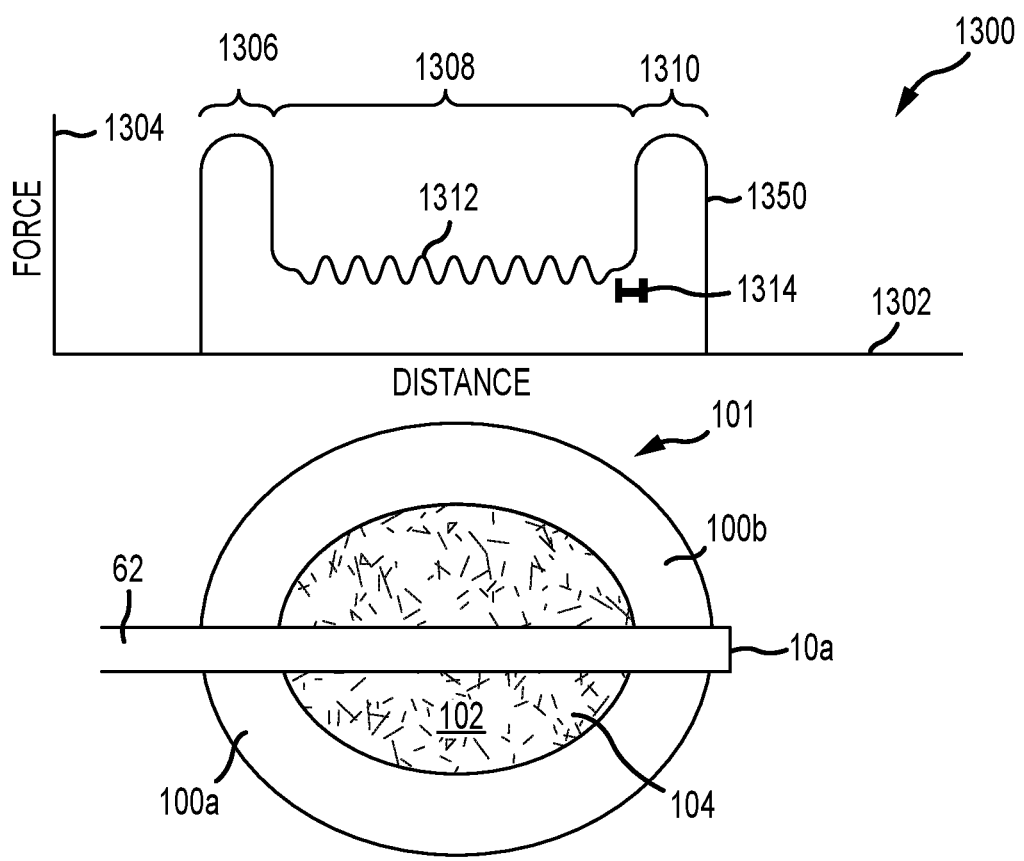
FIG. 13 depicts a plot representing an embodiment of operation of the instrument in relation to a schematic view of the anatomy through which a tool portion is advanced.

However, while the foregoing approaches may assist in determining placement of a tool portion 62 in an idealized environment, it is recognized that complications inherent to practical applications of the measurement system 40 may result in false changes in signals being detected. This may lead to false positives in relation not detection of the position of the working tool 62. That is, the foregoing plots shown in FIGS. 11 and 12 may correspond to idealized systems in which the respective signal outputs analyzed are relatively free from noise and other signal artifacts. FIG. 13, in contrast, includes a plot 1300 that is representative of a tool drive signal 1350 that represents an output of a force sensor 50 as a tool portion 62 is advanced relative to a bone 101. In FIG. 13, the plot 1300 is arranged relative to a representation of a bone 101 such that the distance axis 1302 corresponds to the relative structure shown in the bone 101 positioned below the plot 1300. The tool drive signal 1350 of the force sensor 50 is represented relative to a force axis 1304.

The tool drive signal 1350 may have a first portion 1306 that corresponds to the tool portion 62 passing through the first portion of the hard outer cortex 100a. The tool drive signal 1350 may have a second portion 1308 corresponding to the tool portion 62 passing through the medullary layer 102 of the bone 101. The tool drive signal 1350 may have a third portion 1310 corresponding to the tool portion 62 passing through the second portion of the hard outer cortex 100b. As may be appreciated, the first portion 1306 and third portion 1310 of the signal may include a sharp increase in the measured force as represented in the tool drive signal 1350 resulting from the tool portion 62 passing through the relatively dense and hard outer cortex 100. The second portion 1308 may result in a lower force that is relatively constant as the tool portion 62 passes through the medullary layer 102.

While the tool drive signal 1350 is shown as corresponding to a force sensor in FIG. 13, it may be appreciated that in various other contexts, alternative sensors may be used to measure and output tool drive signals corresponding to alternative tool drive parameters for use in determining placement of the leading edge 10a of the tool portion 62. For instance, the measured tool drive parameter and corresponding tool drive signal may include torque, an electrical characteristic of the drive system 30 (e.g., resistance or the like), or other parameters that are characteristic of the advancement of the tool portion 62 relative to the anatomy of a patient. In the regard, appropriate sensors may be provided including torque sensors, resistance detection sensors, or the like.

In many contexts, such tool drive signals will be subjected to noise or other variations from a variety of sources as described above. For instance, certain surgeons may advance a tool portion 62 in a manner that may result in false positive detection of characteristics associated with placement of a tool portion 62. As described above, this may include "pecking" the tool portion 62 with short, rapid advancements relative to the anatomy of the patient. Further still, the anatomy itself may present difficulties. For instance, a medullary layer 102 of a bone may not be uniform. Rather, as shown in FIG. 13, the medullary layer 102 may include trabeculae 104. Trabeculae 104 include a network of osseous tissue that may be present in the medullary layer 102.

In any regard, the resulting tool drive signal 1350 may have localized peaks 1312 in the signal. As may be appreciated, when monitoring for an increase in the tool drive signal 1350, such localized peaks 1312 may be detected and result in false detections of either positive or negative changes in the tool drive signal. As described above, the localized peaks 1312 may be a result of either the anatomy of the patient (e.g., resulting from encountering trabeculae 104) or the manner in which the tool portion 62 is advanced. In any regard, the localized peaks 1312 may represent a relatively brief (e.g., with respect to displacement 1302 or time) increase in the tool drive signal 1350. As such, these localized peaks 1312 are preferably disregarded when analyzing the tool drive signal 1350 in relation to any of the placement techniques described above in relation to FIGS. 6-9.

Accordingly, the controller 146 may monitor the drive output signal 1350 to determine a change in the tool drive parameter (e.g., force) as represented in the tool drive signal 1350 relative to a given amount of axial displacement 1314 of the tool 62. Note that while a given amount of axial displacement 1314 is represented in FIG. 13 as an example of one such given displacement 1314, FIG. 13 is not to scale and the actual relation of the given displacement 1314 relative to the signal 1350 is not represented. The identification of a change in the tool drive signal 1350 relative to the given displacement 1314 may be accomplished by a number of different potential approaches.

For instance, the controller 146 may apply a filter to the signal 1350 with a smoothing factor that results in any localized peaks 1312 being reduced or eliminated. As an example, the filter may comprise a low pass filter with a cutoff frequency tuned to disregard fast changing frequencies in the signal. Moreover, the signal 1350 may be filtered relative to the axial displacement of the tool portion 62 rather than time, such that the cutoff frequency corresponds to changes in the signal 1350 that only occur over relatively short axial displacement such as less than the given displacement 1314. Accordingly and as may be appreciated, the smoothing factor may be related to the given displacement 1314. Moreover, the given displacement 1314 may be selected or determined based on a characteristic of a tool portion 62 and/or operation performed utilizing the tool portion 62. In any regard, changes in the signal 1350 that occur only over distances less than the given displacement 1314 may be filtered or disregarded in relation to the signal analysis used to determine placement of the tool portion 62.

Figure 15:
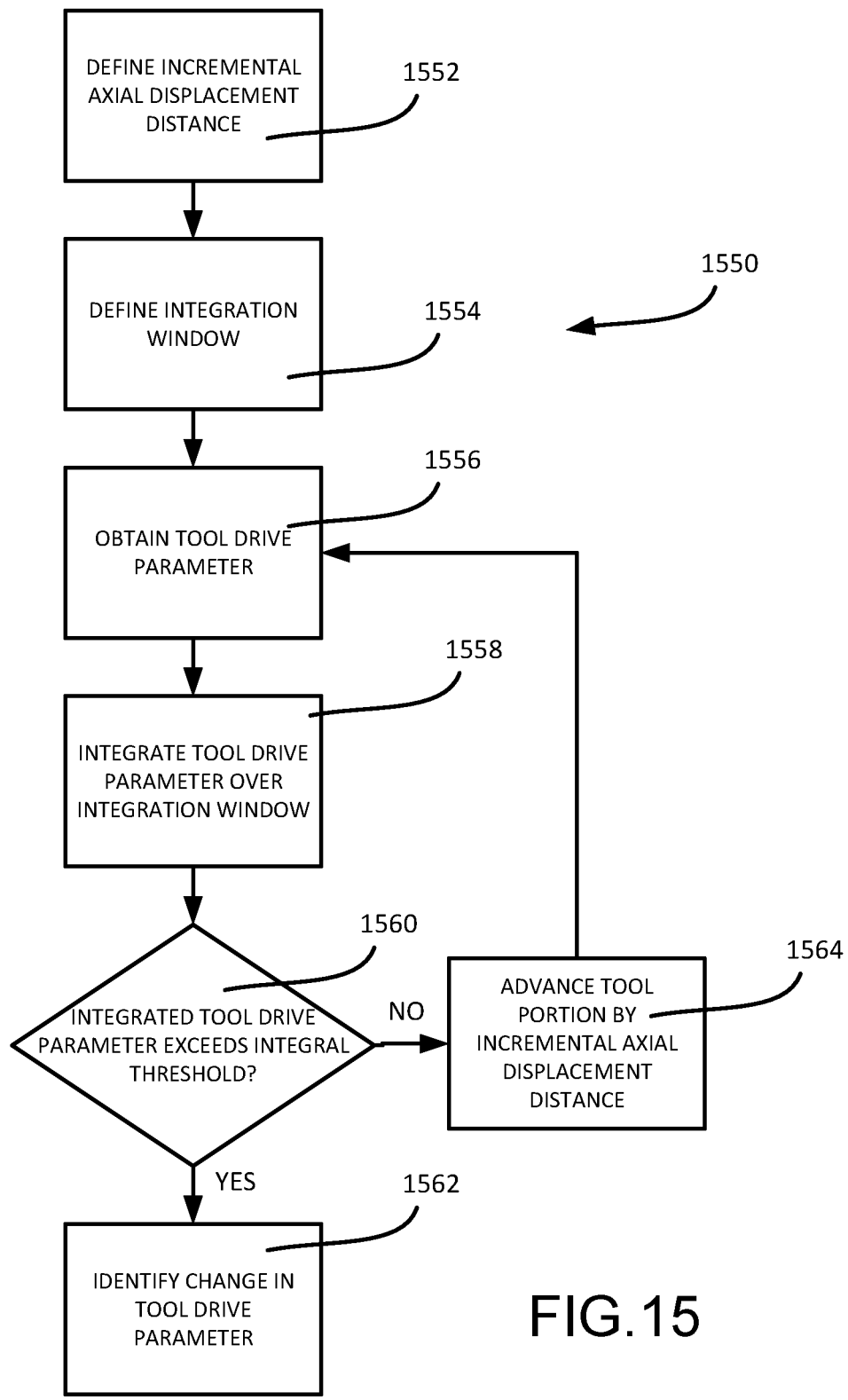
FIG. 15 is a flowchart of an embodiment of an approach to detection of a change in a tool drive parameter.
Figure 16:
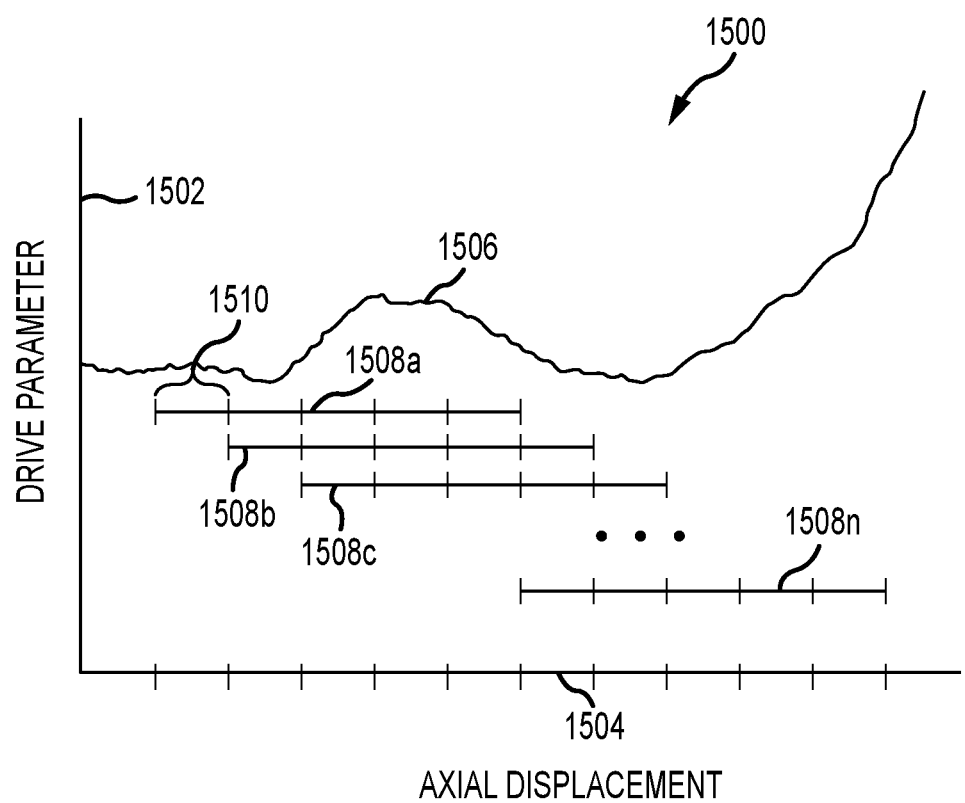
FIG. 16 is a plot depicting the tool drive parameter and analysis according to the embodiment of the approach depicted in FIG. 15.

Another approach is described in relation to FIGS. 15 and 16. This approach may include integrating a tool drive signal 1506 to identify a change in the signal as described above. That is, this approach may be used in connection with any of the placement modes described above in relation to FIGS. 6-9. That is, where a change in the tool drive parameter 1506 is to be monitored (e.g., for an increase or a decrease), the following approach may be utilized to detect such a change in the tool drive parameter 1506. As may be appreciated, this approach may analyze the tool drive parameter 1506 in relation to axial displacement rather than time such that the analysis is not dependent on or performed in relation to time.

A method 1400 for identifying a change in the tool drive parameter 1506 is shown in FIG. 15 and will be described in relation to FIG. 16 that includes a plot 1500 of the tool drive parameter 1506. The plot 1500 includes a vertical axis 1502 representative of the drive parameter value and a horizontal axis 1504 representative of axial displacement of the tool portion 62. As can be appreciated, the tool drive parameter 1506 may comprise a signal having noise that experiences variations that may not be attributable to the tool portion 62 passing between mediums.

In turn, the method 1550 may include defining 1552 an incremental axial displacement distance 1510. The incremental axial displacement distance 1510 may correspond to the given amount of axial displacement referenced above. The method 1550 may also include defining 1554 an integration window 1508. The integration window may comprise a plurality of incremental axial displacement distances 1510 to define the magnitude of the integration window 1508. For instance, in FIG. 16, five incremental axial displacement distances 1510 may comprise an integration window 1508, however other numbers of incremental axial displacement distances 1510 may be chosen to comprise the integration window 1508 without limitation. As can also be appreciated in FIG. 16, a plurality of integration windows 1508a, 1508b, 1508c, . . . 1508n may be defined. In turn, the method 1550 may include obtaining 1556 the tool drive parameter 1506 (e.g., as a signal output from a sensor on the instrument 10).

The method 1550 may include integrating 1558 the tool drive parameter 1506 over a first integration window 1508a to generate an integrated tool drive parameter. The integrated tool drive parameter may comprise the summed value of the tool drive parameter 1506 over the integration window 1508. This may represent the area under the curve representative of the tool drive parameter 1506 shown in FIG. 16. For instance, in FIG. 16, as the tool drive parameter 1506 is obtained for the first integration window 1508a, the integral of the tool drive parameter 1506 may be determined by summing the tool drive parameter 1506 over each of the incremental axial displacement distances 1510 in the first integration window 1508a.

The method 1550 may also include comparing 1560 the integrated tool drive parameter to an integral threshold. If the integrated tool drive parameter does not exceed the integral threshold, the method 1550 may include advancing 1564 the tool portion by an incremental axial displacement distance 1510 and obtaining 1556 additional tool drive parameter 1506 data. For instance, if the integrated tool drive parameter does not exceed the integral threshold within integration window 1508a, the tool may be advanced 1564 by an incremental axial displacement distance 1510 to define a new integration window 1508b. As may be appreciated, while additional tool drive parameter 1506 data is shown distal to the first integration window 1508a relative to the axial displacement 1504, when collecting in real time, the first integration window 1508a may correspond to the most recent tool drive parameter 1506 data collected. As such, tool drive parameter data 1506 may be collected as the integration window 1508 is advanced such that the current integration window 1508 may represent the most distal portion of the tool drive parameter 1506 data. Accordingly, integration windows 1508a, 1508b, and 1508c represent historical windows in FIG. 16 for purposes of illustration.

This process may repeat at 1508c and so forth. However, returning to the comparing 1560, if the integrated tool drive parameter exceeds the integral threshold, then the method 1550 may include identifying 1562 a change in the tool drive parameter 1506. This identification 1562 of the change in the tool drive parameter 1506 may be used in conjunction with any process for determining the tool portion 62 passing from one medium to another medium. Such an identification 1562 may occur as shown in FIG. 16 at 1508n, which is the nth integration window in which the integrated tool drive parameter for the integration window 1508n exceeds the integration threshold based on the increase in the tool drive parameter 1506. As can be appreciated, the tool drive parameter 1506 also experienced an increase in the integration windows 1508a, 1508b, and 1508c. However, this increase was not significant over the totality of each of the integration windows to exceed the integration threshold. This demonstrates this approach's ability to filter out changes in the tool drive parameter 1506 that are not significant events to avoid false detection.

Additionally or alternatively, the controller 146 may be operative to calculate a moving average of the signal 1350 relative to the axial displacement measure 1302. That is, the moving average may be calculated by averaging values of the signal 1350 over the given displacement 1314. In turn, a change in the tool drive parameter may be identified for determination or identification of tool portion 62 placement in response to identification of an inflection of the moving average (e.g., including when the derivative of the moving average moves from positive to negative or negative to positive depending on the context). As will be appreciated in the discussion to follow, the moving average may be calculated for the tool drive parameter relative to axial displacement rather than relative to time. In this regard, the tool drive parameter may be analyzed without respect to time as the moving average may be calculated relative to axial displacement.

For instance, when the tool portion 62 moves from a medullary layer 102 of the bone 101 to a cortex layer 100 of the bone 101, the moving average may experience an inflection corresponding to a minimum in the moving average. Alternatively, when the tool portion 62 moves from a cortex layer 100 of the bone 101 to a medullary layer 102 of the bone 101, the moving average may experience an inflection corresponding to a maximum in the moving average.

It may be appreciated that the given distance 1314 over which a change in the signal 1350 must occur to be recognized in relation to the analysis of the signal 1350 for determining placement of the tool portion 1314 may vary based on the context. However, in at least some embodiments, the given distance 1314 may be at least about 0.5 mm. In other embodiments, the given distance 1314 may preferably be about 1.0 mm. In further embodiments, the given distance 1314 may be at least about 1.5 mm, 2.0 mm, 2.5 mm, or even 3 mm.

Figure 17:
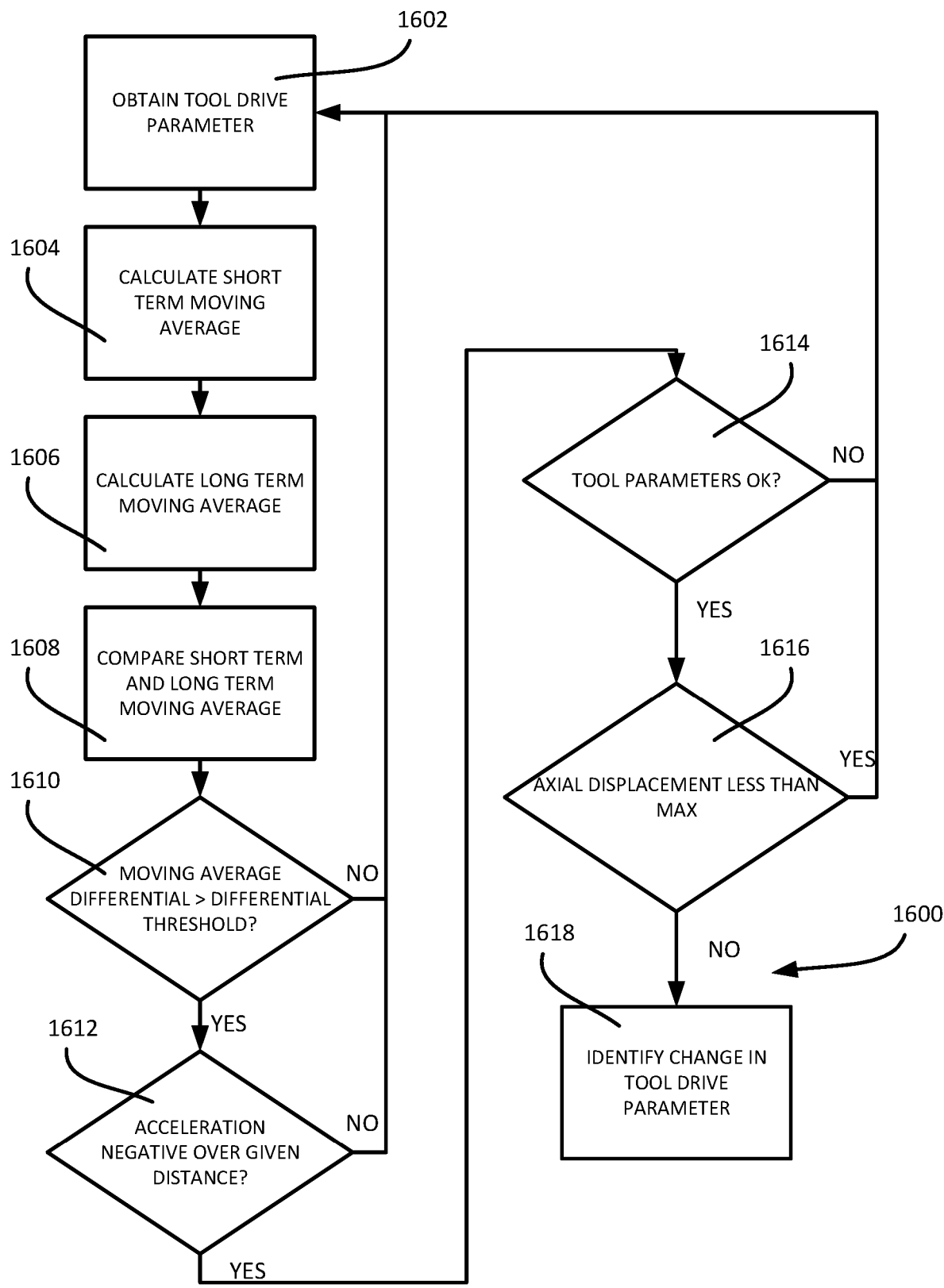
FIG. 17 is a flowchart of an embodiment of an approach to detection of a change in a tool drive parameter.
Figure 18:
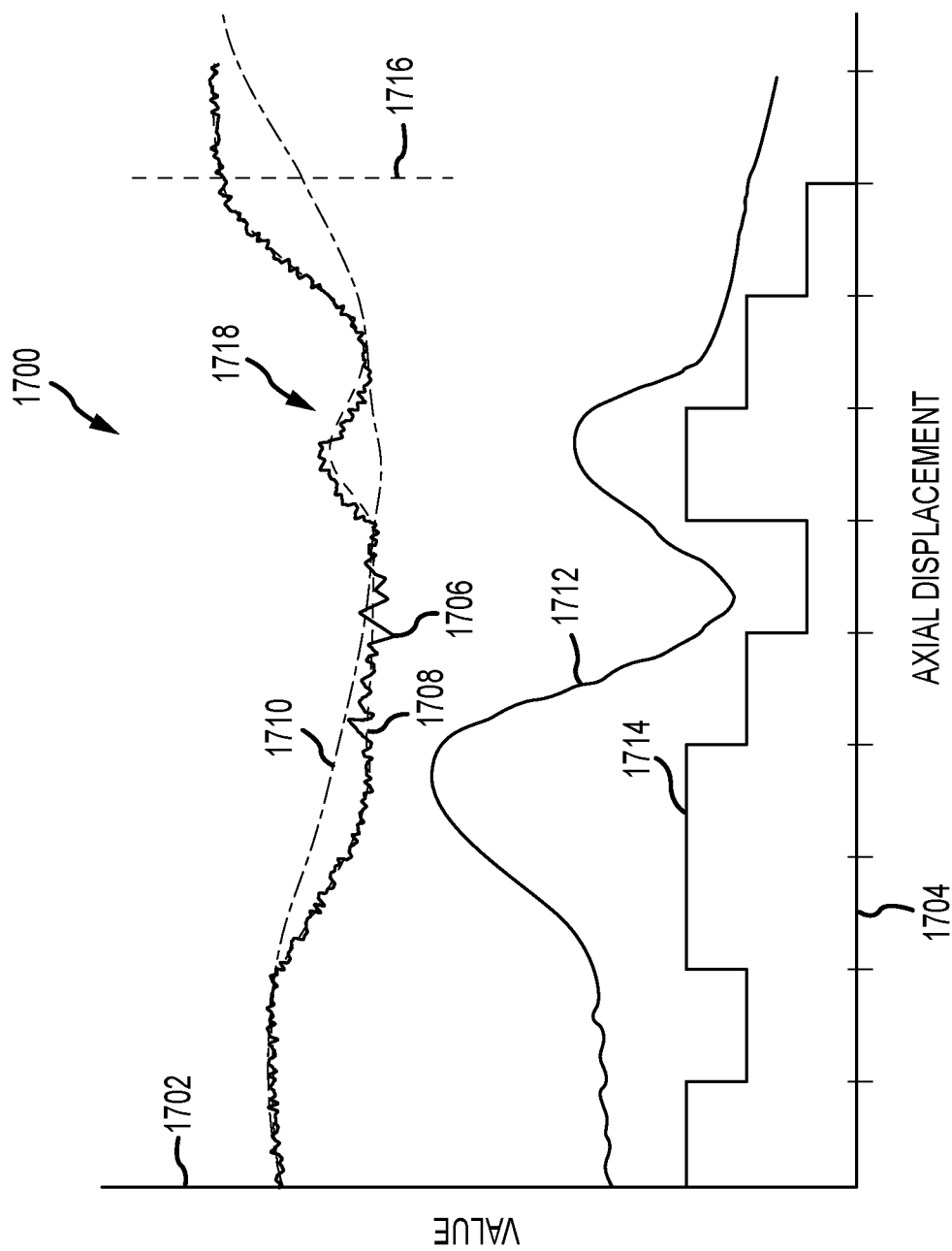
FIG. 18 is a plot depicting the tool drive parameter and analysis according to the embodiment of the approach depicted in FIG. 17.

Still a further approach that may employ moving averages is described in relation to FIGS. 17 and 18. FIG. 17 depicts a method 1600 that may utilize the calculation of two moving averages and comparison of the moving averages relative to one another. FIG. 18 depicts a plot 1700 showing various signals that may be used in the method 1600. The vertical axis 1702 of the plot 1700 may represent a value of various parameters monitored or calculated in the method 1600. The horizontal axis 1704 may correspond to the axial displacement of the tool portion 62. Like the moving average approach described above, the two moving averages may be calculated relative to axial displacement rather than time such that the tool drive parameter may be monitored without regard to time.

The method 1600 may begin by obtaining 1602 a tool drive parameter 1706. As can be appreciated from the plot 1700, the tool drive parameter 1706 may include some noise in the signal. As such, the method 1600 may include calculating 1604 a short term moving average 1708. In addition, the method 1600 may include calculating 1606 a long term moving average 1710. The short term moving average 1708 may be calculated 1604 using tool drive parameter values over a first increment (e.g., related to a first axial displacement of the leading edge of the tool portion) that is smaller than a second increment (e.g., related to a second axial displacement of the leading edge of the tool portion) over which the long term moving average 1710 is calculated 1606. As described above, the increment over which the moving averages are calculated may be with respect to axial displacement such that sampled values of the tool drive parameter 1706 over each respective increment of axial displacement is used to calculate the respective average. Alternatively, the increment may be relative to time. In either regard, the long term moving average 1710 may include more values of the tool drive parameter 1706 than the short term moving average 1708. In this regard, the short term moving average 1708 may capture more rapid changes in the tool drive parameter 1706 while the long term moving average 1710 may reflect only changes in the tool drive parameter 1706 that occur over a longer axial displacement.

As such, the method 1600 may include comparing 1608 the short term moving average 1708 to the long term moving average 1710. As can be appreciated in the plot 1700, as the leading edge 10a of the tool portion 62 transitions form one medium to another, the tool drive parameter 1706 may rise (e.g., the force on the tool portion 62 may increase). As shown in the plot 1700, the short term moving average 1708 may relatively closely track the increase in the tool drive parameter 1706, while the long term moving average 1710 may lag the tool drive parameter 1706. Accordingly, at the comparing 1610, if the short term moving average 1708 differs from the long term moving average 1710 by greater than a differential threshold, the method 1600 may progress as described in greater detail below. If the differential threshold is not exceeded, the method 1600 may turn to obtaining 1602 the tool drive parameter 1706. For instance, as can be seen in FIG. 18, there is a short term rise 1718 in the tool drive parameter 1706 prior to the identified change 1716. In this area, while the short term moving average 1708 may deviate from the long term moving average 1710, the differential did not exceed the differential threshold such that no change was identified. However, at 1716, the differential exceeded the differential threshold, thus indicating the change 1718.

The method 1600 may also include other checks to ensure that an identified change in the tool drive parameter 1706. For instance, the method 1600 may also include checking 1612 an acceleration signal 1714. The displacement sensor 42 may allow for a calculation of a velocity signal 1712 (e.g., by calculating a first derivative of the displacement). The velocity signal 1712 may be sampled at a given amount of axial displacement to determine if the tool portion is accelerating (velocity is increasing) or decelerating (velocity is decreasing). This acceleration indication may be determined by taking the derivative of the velocity signal 1712. The acceleration signal 1714 may indicate how many consecutive samples in which the tool portion 62 has decelerated. The consecutive samples may comprise an average of the acceleration over a given axial displacement. The check 1612 may include determining that a threshold number of samples in which there is deceleration occurs prior to determining a change. For instance, in the plotted example, that threshold number of deceleration samples may be three. As such, the acceleration signal 1714 may be at an initial value of three and reduced by one each time a sample is taken in which a declaration is detected from the velocity signal 1714. If the tool portion 62 accelerates (e.g., undergoes positive acceleration rather than negative acceleration referred to herein as deceleration) at any sample, the value of the acceleration signal 1714 may be reset to the initial value. Accordingly, as can be appreciated at the detected change 1716, both the differential threshold may be exceeded and the deceleration value may be 0, indicative of three consecutive samples in which the tool portion 62 has decelerated. In contrast, even in the short term rise 1718 area of the plot 1700, if the differential threshold had been exceeded, a change would not have been detected because check 1612 would have indicated that the acceleration signal 1714 had not had a sufficient number of consecutive instances of deceleration.

The method 1600 may also include checking 1614 a number of tool parameters. These tool parameters may include determinations that the instrument is active (e.g., the trigger for advancing the instrument is depressed and the motor of the instrument is running) upon occurrence of the identification of the differential in the moving average exceeding the differential threshold. The tool parameters observed in the checking 1614 may also include determining if the drill is "zeroed" or reset when the leading edge 10a of the working portion 62 is coplanar with a reference surface of a displacement sensing arm. This checking 1614 may also include observing the one or more sensors of the instrument 100 to determine if the sensor outputs are in a given acceptable range (e.g., prior to operation or during operation). The method 1600 may also include checking 1616 that the axial displacement of the tool portion 62 is greater than the previous max displacement at the occurrence of the change. For instance, if the tool portion 62 had been retracted and advanced again and the detection of the change occurred in a location of the axial displacement that was less than the maximum displacement (e.g., in a region in which the tool is readvanced) the change may be ignored and the method 1600 may continue to obtain 1602 the tool drive parameter. However, if all of the foregoing additional checks are satisfied, then the method 1600 may include identifying 1618 a change in the tool drive parameter.

Figure 14:
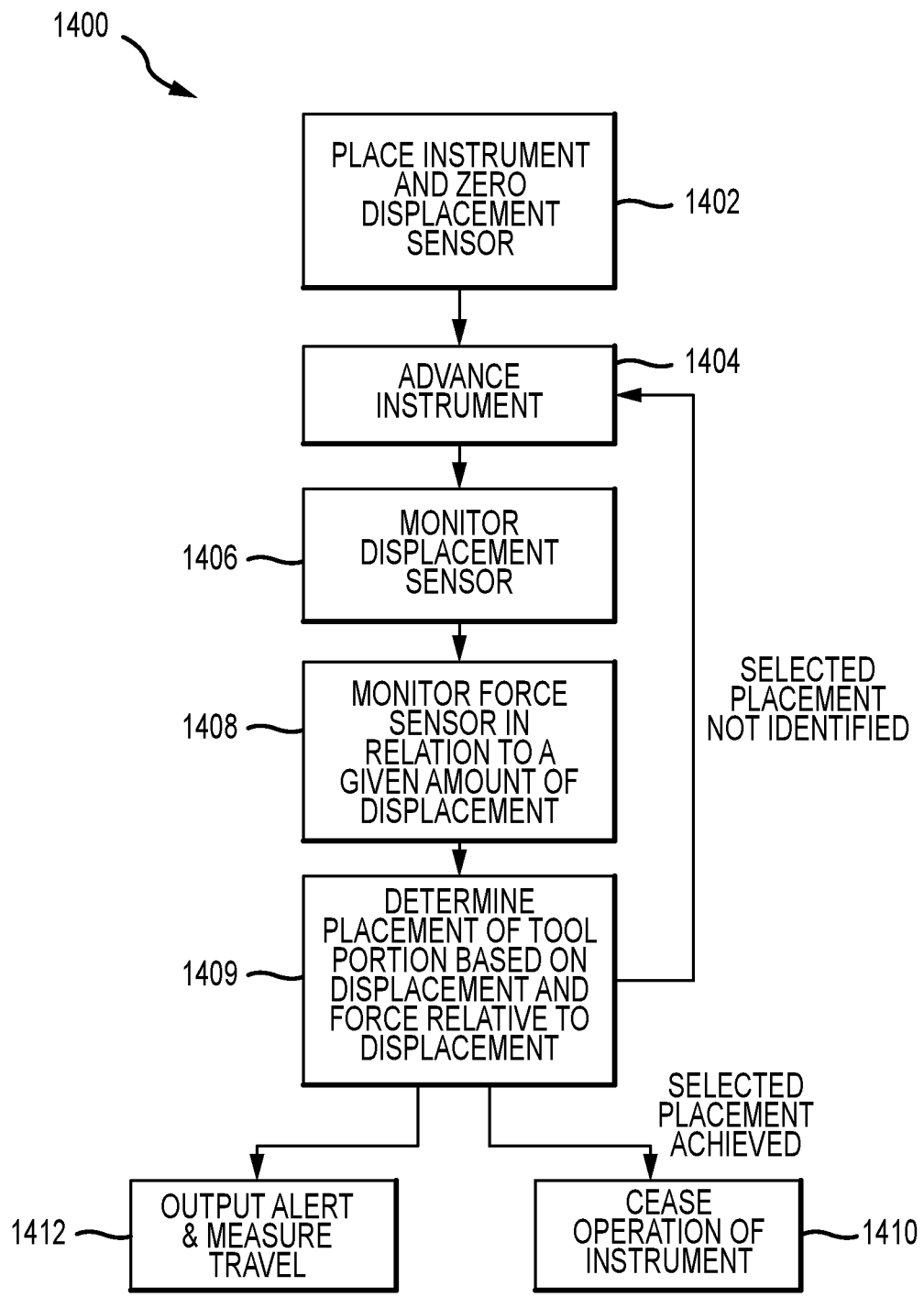
FIG. 14 is a flowchart of an embodiment of a method for operation of an instrument.

With further reference to FIG. 14, a flowchart is shown depicting an embodiment of a method 1400 in which the instrument 10 described above may be utilized. The method 1400 may include placing 1402 the instrument 10 relative to the anatomy of the patient to be operated upon. Once the instrument 10 has been placed 1402, the displacement sensor 42 of the instrument 10 may be zeroed (e.g., through interaction with the controller 146). Thereafter, the method 1400 may include advancing 1404 the instrument 10, specifically the tool portion 62, relative to the anatomy of the patient. In this regard, a user may initiate operation of the instrument 10 (e.g., by selecting the appropriate trigger 90/92) advancing the leading edge 10a of the tool portion 62.

The method 1400 may further include monitoring 1406 the displacement sensor 42. The monitoring 1406 may include communicating an output of the displacement sensor 42 to the controller 146. The method 1400 may also include monitoring 1408 the force sensor 50 in relation to a given amount of displacement 1314. As described above, any or all of the approaches to monitoring 1408 the force sensor in relation to a given amount displacement 1314 may be utilized. Accordingly, the method 1400 may include determining 1409 placement of the tool portion based on the displacement signal and the force signal as analyzed relative to the displacement. If the selected placement is not identified, the method 1400 may iterate such that the instrument 10 is continued to be advanced 1404. However, if the selected placement is achieved, the method may include ceasing 1410 operation of the instrument 10. Additionally or alternatively, the method 1400 may include outputting 1412 one or more alerts and/or measuring the travel of the tool portion 62 upon the selected placement being achieved. By the selected placement, it is meant the designated placement of the tool portion 62 based on the specific characteristics of the displacement sensor 42 and force sensor 50 in relation to a given amount displacement for a given mode as identified based on the mode that has been selected at the controller 146.

Accordingly, the foregoing disclosure includes details regarding systems and methods that may be used for improved placement of a tool portion 62 of a powered instrument 10. Specifically, the foregoing approaches provide the ability to accurately place the tool portion 62 relative to specific portion of anatomy of the patient as selected by the user selection of a mode at the controller 146. The placement may specifically be determined based on analysis of a tool drive signal 1350 relative to a given amount of axial displacement of the leading edge 10a of the tool 62 such that noise and/or other artifacts in the tool drive signal 1350 may be disregarded to avoid false indications of placement resulting from such noise and/or other artifacts. In turn, more accurate, reliable, and/or repeatable operation of the instrument 10 may be provided.

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences). Accordingly, it should be understood that only the preferred embodiment and variants thereof have been shown and described and that all changes and modifications that come within the spirit of the invention are desired to be protected.

What is claimed is:

1. A measurement system for use with a powered surgical instrument for sensing a position of a leading edge of a tool portion relative to anatomic structures of a patient, the measurement system comprising:
    a first sensor disposed with respect to the powered surgical instrument to measure a tool drive parameter that is characteristic of the tool portion acting on the patient and output a tool drive signal representative of the tool drive parameter as the tool portion is advanced relative to anatomy of the patient;
    a displacement sensor disposed with respect to the powered surgical instrument to measure an axial displacement of the leading edge of the tool portion relative to a reference point and output a displacement signal representative of the axial displacement; and
    a controller in operative communication with the first sensor to receive the tool drive signal and in operative communication with the displacement sensor to receive the displacement signal, wherein the controller is operative to identify a change in the tool drive parameter over a given amount of axial displacement of the leading edge of the tool portion that is indicative of the leading edge of the tool portion moving through an interface between anatomic structures of the patient, and wherein the controller is operative to determine an integrated tool drive parameter comprising a sum of the tool drive parameter over a given plurality of instances of the given amount of axial displacement of the leading edge of the tool portion.

2. The measurement system of claim 1, wherein the given amount of axial displacement of the leading edge of the tool portion is at least 0.1 mm.

3. The measurement system of claim 1, wherein the controller is in control of an operation of a drive motor of the powered surgical instrument and is operative to stop the drive motor in response to identifying the interface between anatomic structures of the patient.

4. The measurement system of claim 1, wherein the tool drive parameter comprises one of an axial force acting on the tool portion, a torque acting on the tool portion, or an electrical characteristic of a drive motor of the powered surgical instrument.

5. The measurement system of claim 1, wherein the anatomic structures of the patient have different densities.

6. The measurement system of claim 1, wherein the interface through which the leading edge of the tool moves is from a medullary layer of a bone to a cortex layer of the bone.

7. The measurement system of claim 1, wherein the controller is operative to compare the integrated tool drive parameter to an integral threshold value and identify a change in the tool drive parameter when the integrated tool drive parameter exceeds the integral threshold value.

8. The measurement system of claim 1, wherein the given plurality of instances of the given amount of axial displacement of the leading edge of the tool portion comprise immediately preceding instances of the given amount of axial displacement to a current position of the leading edge of the tool portion.

9. The measurement system of claim 1, wherein the given amount of axial displacement comprises 0.1 mm and the given plurality of instances comprises ten instances.

10. The measurement system of claim 1, wherein the controller is operative to monitor for a change in the tool drive parameter when the leading edge of the tool portion decelerates in three consecutive instances of the given amount of axial displacement of the leading edge of the tool portion.

11. The measurement system of claim 10, wherein the controller is operative to determine deceleration in the leading edge based on the displacement signal by calculating a second derivative of the displacement signal.

12. A method for use with a powered surgical instrument for sensing a position of a leading edge of a tool portion relative to anatomic structures of a patient, the method comprising:
    measuring a tool drive parameter that is characteristic of the tool portion acting on the patient as the tool portion is advanced relative to anatomical structures of the patient at a first sensor of the powered surgical instrument;
    outputting a tool drive signal representative of the tool drive parameter;
    measuring at a displacement sensor of the powered surgical instrument an axial displacement of the leading edge of the tool portion relative to a reference point;
    outputting a displacement signal representative of the axial displacement;
    monitoring the tool drive signal and the displacement signal as the leading edge of the tool portion is advanced relative to the anatomical structures of the patient;
    determining an integrated tool drive parameter comprising a sum of the tool drive parameter over a given plurality of instances of a given amount of axial displacement of the leading edge of the tool portion; and
    identifying a change in the tool drive parameter over the given amount of axial displacement of the leading edge of the tool portion that is indicative of the leading edge of the tool portion moving through an interface between anatomic structures of the patient based on the integrated tool drive parameter.

13. The method of claim 12, wherein the given amount of axial displacement of the leading edge of the tool portion is at least 0.1 mm.

14. The method of claim 12, further comprising:
    stopping operation of a drive motor of the powered surgical instrument in response to the identifying.

15. The method of claim 12, wherein the tool drive parameter comprises one of an axial force acting on the tool portion, a torque acting on the tool portion, or an electrical characteristic of a drive motor of the powered surgical instrument.

16. The method of claim 12, wherein the anatomic structures of the patient have different densities.

17. The method of claim 12, wherein the interface through which the leading edge of the tool moves is from a medullary layer of a bone to a cortex layer of the bone.

18. The method of claim 12, further comprising:
comparing the integrated tool drive parameter to an integral threshold value; and
identifying the change in the tool drive parameter when the integrated tool drive parameter exceeds the integral threshold value.

19. The method of claim 12, wherein the given amount of axial displacement comprises 0.1 mm and the given plurality of instances comprises ten instances.

20. The method of claim 12, further comprising:
monitoring for a change in the tool drive parameter when the leading edge of the tool portion decelerates in three consecutive instances of the given amount of axial displacement of the leading edge of the tool portion.

21. The method of claim 20, further comprising:
determining deceleration in the leading edge based on the displacement signal by calculating a second derivative of the displacement signal.

\* \* \* \* \*